US010962527B2

(12) United States Patent
Blainey et al.

(10) Patent No.: US 10,962,527 B2
(45) Date of Patent: Mar. 30, 2021

(54) MULTI-STAGE, MULTIPLEXED TARGET ISOLATION AND PROCESSING FROM HETEROGENEOUS POPULATIONS

(71) Applicants: THE BROAD INSTITUTE, INC., Cambridge, MA (US); MASSACHUSETTS INSTITUTE OF TECHNOLOGY, Cambridge, MA (US); THE GENERAL HOSPITAL CORPORATION, Boston, MA (US); Paul Blainey, Cambridge, MA (US); Dwayne Vickers, San Diego, CA (US); Nir Hacohen, Brookline, MA (US)

(72) Inventors: Paul Blainey, Cambridge, MA (US); Dwayne Vickers, San Diego, CA (US); Nir Hacohen, Brookline, MA (US)

(73) Assignees: THE BROAD INSTITUTE, INC., Cambridge, MA (US); MASSACHUSETTS INSTITUTE OF TECHNOLOGY, Cambridge, MA (US); THE GENERAL HOSPITALL CORPORATION, Boston, MA (US)

( * ) Notice: Subject to any disclaimer, the term of this patent is extended or adjusted under 35 U.S.C. 154(b) by 7 days.

(21) Appl. No.: 16/075,258

(22) PCT Filed: Feb. 3, 2017

(86) PCT No.: PCT/US2017/016546

§ 371 (c)(1),
(2) Date: Aug. 3, 2018

(87) PCT Pub. No.: WO2017/136751

PCT Pub. Date: Aug. 10, 2017

(65) Prior Publication Data

US 2019/0049434 A1 Feb. 14, 2019

Related U.S. Application Data

(60) Provisional application No. 62/292,074, filed on Feb. 5, 2016.

(51) Int. Cl.
*G01N 33/50* (2006.01)
*G01N 33/536* (2006.01)
(Continued)

(52) U.S. Cl.
CPC .... *G01N 33/5044* (2013.01); *B01L 3/502715* (2013.01); *B01L 3/502761* (2013.01);
(Continued)

(58) Field of Classification Search
None
See application file for complete search history.

(56) References Cited

U.S. PATENT DOCUMENTS 8,765,391 B2 * 7/2014 Zaugg .............. G01N 33/54326 435/7.24
9,394,511 B2 * 7/2016 Jiang ...................... C12M 47/04
(Continued)

FOREIGN PATENT DOCUMENTS

WO 2014153651 A1 10/2014

OTHER PUBLICATIONS

Lee Hun Joo, et al., "Efficient Isolation and Accurate in Situ Analysis of Circulating Tumor Cells Using Detachable Beads and a High-Pore-Density Filter", Angewandte Chemie (International Ed. in English) Aug. 5, 2013, vol. 52, No. 32.
(Continued)

*Primary Examiner* — Changhwa J Cheu
(74) *Attorney, Agent, or Firm* — Burns & Levinson LLP; Christopher R. Cowles

(57) ABSTRACT

A system and method for isolating target substrates includes a microfluidic chip, comprising a plurality of processing
(Continued)

units, each processing unit comprising: an inlet port, a plurality of first chambers connected to the inlet port by a fluid channel, the fluid channel comprising a plurality of valves, a plurality of second chambers, each of the second chambers connected to a respective first chamber by a fluid channel, each fluid channel including a controllable blocking valve, and a plurality of respective outlet ports, each outlet port in fluid communication with a respective one of said second chambers and each outlet port including a blocking valve. A magnet is adjacent the microfluidic chip and is movable relative to the microfluidic chip. A valve control is capable of actuating certain ones of the controllable blocking valves in response to a control signal.

12 Claims, 30 Drawing Sheets

(51) Int. Cl.
*G01N 33/58* (2006.01)
*G01N 33/543* (2006.01)
*B01L 3/00* (2006.01)

(52) U.S. Cl.
CPC ......... *G01N 33/536* (2013.01); *G01N 33/543* (2013.01); *G01N 33/54326* (2013.01); *G01N 33/58* (2013.01); *B01L 2300/0861* (2013.01); *G01N 33/587* (2013.01)

(56) References Cited

U.S. PATENT DOCUMENTS 10,495,634 B2 * 12/2019 Gandini ................ B01L 3/5027
2009/0035746 A1 * 2/2009 Ehben ............... B01L 3/502761 435/4
2012/0270332 A1 * 10/2012 Wimberger-Friedl .... B03C 1/01 436/177
2015/0093745 A1 * 4/2015 Harper ................... G01N 21/07 435/5
2015/0105287 A1 * 4/2015 Lu .................... G01N 33/54326 506/9
2016/0354773 A1 * 12/2016 Li ............................ G01N 1/34

OTHER PUBLICATIONS

International Search Report, International Application No. PCT/US2017/016546; International Filing Date Feb. 3, 2017, Form PCT/ISA/210 (first sheet) (dated Jan. 2015)

Miltenyi S et al: “High Gradient Magnetic Cell Separation With MACS”, Cytometry, Alan Liss, New York, US, vol. 11, Jan. 1, 1990 (Jan. 1, 1990), pp. 231-238, XP002914233, ISSN: 0196-4763, DOI: 10.1002/CYTO.990110203 * (fig 2; abstr; fig 1)*.

Scott M. Berry et al: “Streamlining Immunoassays with Immiscible Filtrations Assisted by Surface Tension”, Analytical Chemistry, vol. 84, No. 13, Jul. 3, 2012 (Jul. 3, 2012), pp. 5518-5523, XP55061397, ISSN: 0003-2700, DOI: 10.1021/ac300085m * (abstr; p. 5518-5519, bridging para) *.

Scott M Berry et al: “Purification of cell subpopulations via immiscible filtration assisted by surface tension (IFAST)”, Biomedical Microdevices, Kluwer Academic Publishers, BO, vol. 13, No. 6, Jul. 28, 2011 (Jul. 28, 2011), pp. 1033-1042, XP019976364, ISSN: 1572-8781, DOI: 10.1007/510544-011-9573-Z * (p. 1035, col. 1, last lines) *.

Jianing Jiang et al: “An integrated microfluidic device for rapid and high-sensitivity analysis of circulating tumor cells”, Scientific Reports, vol. 7, No. 1, Feb. 15, 2017 (Feb. 15, 2017), XP55686992, DOI: 10.1038/srep42612.

European Search Report for European Patent Application No. 17 706 351.8 dated Jan. 27, 2021.

* cited by examiner

| Volume of Beads | Amount of Beads | Purity | Yield |
|---|---|---|---|
| 25uL | 1.00E+07 | 48.15% | 0.3 |
| 20uL | 8.00E+06 | 91.63% | 3.4 |
| 15uL | 6.00E+06 | 89.31% | 3.7 |
| 10uL | 4.00E+06 | 94.79% | 5.8 |
| 5uL | 2.00E+06 | 93.71% | 4.9 |

| Cell Type | Purity (%) | Total Target Cells | Yield (%) |
|---|---|---|---|
| Tube CD4 T Cells | 92 | | |
| Tube CD8+ T Cells | 98 | | |
| Tube B Cells | 97 | | |
| Tube Monocytes | 93 | | |
| Device CD4 T Cells | 95.2 | 4479 | 9.3 |
| Device CD8+ T Cells | 96.7 | 3868 | 8.1 |
| Device B Cells | 95.2 | 1570 | 3.3 |
| Device Monocytes | 93.1 | 15370 | 32 |

Benchtop Control

Nextera XT Tagmentation

Device Control

Adapter Ligand Fragments Amplification

| Volume of Beads | Number of Beads | % purity | Number yield | % yield |
|---|---|---|---|---|
| 25uL | 1.00E+07 | 48.15% | 44 | 0.3 |
| 20uL | 8.00E+06 | 91.63% | 434 | 3.4 |
| 15uL | 6.00E+06 | 89.31% | 478 | 3.7 |
| 10uL | 4.00E+06 | 94.79% | 746 | 5.8 |
| 5uL | 2.00E+06 | 93.71% | 636 | 4.9 |

MULTI-STAGE, MULTIPLEXED TARGET ISOLATION AND PROCESSING FROM HETEROGENEOUS POPULATIONS

RELATED APPLICATIONS AND INCORPORATION BY REFERENCE

This application is the U.S. national stage pursuant to 35 U.S.C. § 371, of United States International Patent Application Ser. No. PCT/US2017/016546, filed Feb. 3, 2017 and published in English on Aug. 10, 2017 as publication WO 2017/136751, which claims benefit of and priority to U.S. provisional patent application 62/292,074 filed Feb. 5, 2016, incorporated herein by reference.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under Grant No. AI118668 awarded by the National Institutes of Health. The government has certain rights in the invention.

FIELD OF THE INVENTION

The present invention relates to a method for isolating cells or other biological components compatible with microfluidic techniques. The present invention is appropriate for initial stage—cells; subsequent stages for 'substrates' as needed for genomic library construction and multiple patient samples and multiple cell types/subsets from each patient sample. The present invention further relates to mixing of such components.

BACKGROUND OF THE INVENTION

The present invention relates to a method for isolating cells or other biological components compatible with microfluidic techniques. Low cost DNA sequencing/next generation sequencing (NGS) is a field of study transforming biomedical science. Sequencing instruments are so effective today that sample preparation is often the limited factor in genomic analysis. In addition, sample quantity requirements prevent the deployment of NGS for applications in clinical diagnostics. As the cost of sequencing has dropped, the cost of sample preparation has increased; where more than 50% of the total cost is related to sample preparation.

For example, to sequence eukaryotic genomes, cells must be lysed and their DNA purified, fragmented, tagged with adaptors, and size-selected before loading on a sequencing instrument. These steps demand significant application of resources including reagents, other consumables, labor, and possibly automation equipment (to mitigate labor costs) that ultimately limit throughput. The introduction of liquid handling robotics and electrowetting-based "digital" microfluidics have helped to increase throughput, but these workflows require high DNA input, do not integrate all the key workflow steps (variously omitting cell lysis, DNA fragmentation, and size selection), and substantially offset reductions in reagent and labor costs with expensive proprietary equipment and consumables.

To address this issue, Applicants have provided a microfluidic sample preparation platform that efficiently utilizes input biomass and integrates the key steps in cells-to-sequence library sample preparation for up to 30 samples while maintaining or improving data quality. Thus, the microfluidic system has a general-purpose microarchitecture able to run workflows with arbitrary numbers of selection, reaction, pull-down, and cleanup steps. Applicants demonstrate how integrated lab-on-chip sample preparation addresses key barriers in eukaryotic genomics to enable improved genomics analyses across a broad range of basic and translational applications.

Cells come in different types, sub-types and activity states, which are classified based on their shape, location, function, or molecular profiles, such as the set of RNAs that they express. RNA profiling is in principle particularly informative, as cells express thousands of different RNAs. Approaches that measure for example the level of every type of RNA have until recently been applied to "homogenized" samples—in which the contents of all the cells are mixed together. Methods to profile the RNA content of tens and hundreds of thousands of individual human cells have been recently developed, including from brain tissues, quickly and inexpensively. To do so, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. See, e.g., U.S. 62/048,227 filed Sep. 9, 2014.

Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to $10^8$ discrete biological entities (including, but not limited to, individual cells or organelles) to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

Drop-Sequence methods and apparatus provides a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read. A combination of molecular barcoding and emulsion-based microfluidics to isolate, lyse, barcode, and prepare nucleic acids from individual cells in high-throughput is used. Microfluidic devices (for example, fabricated in polydimethylsiloxane), sub-nanoliter reverse emulsion droplets. These droplets are used to co-encapsulate nucleic acids with a barcoded capture bead. Each bead, for example, is uniquely barcoded so that each drop and its contents are distinguishable. The nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells. Single-cell approaches could use any bead type. The present non-single-cell approach can use magnetic or non-magnetic beads Isolating specific cell types is often desirable for clinical diagnostic and therapeutic applications. In the clinical diagnostics field, there is a need, for example, for morphological analysis of tumor cells, fetal karyotyping, and tissue typing procedures. Therapeutically, there is a need, for example, for purging cells or tissues intended for use in autologous cellular or tissue transfusions or transplantations, e.g. purging tissues of viral antigens and tumor cells. There is also a need for enriching or isolating desirable cells for use in transplantations, e.g. for use in ex vivo expansion of hematopoietic cells intended for allogeneic and autologous transplantation, and for the use in adoptive immunotherapy of potent antigen presenting cells (dendritic cells), cytotoxic T lymphocytes, natural killer (NK) cells and natural suppressor cells.

Once cells are separated, they can be lysed and RNA sequencing performed. Creation of a sequence library can change from platform to platform in high throughput sequencing. There are commonalities within each technology. Frequently, in mRNA analysis the 3' polyadenylated (poly(A)) tail is targeted in order to ensure that coding RNA is separated from noncoding RNA. This can be accomplished simply with poly (T) oligos covalently attached to a given substrate.

Due to the 5' bias of randomly primed-reverse transcription as well as secondary structures influencing primer binding sites, hydrolysis of RNA into 200-300 nucleotides prior to reverse transcription reduces both problems simultaneously. However, there are trade-offs with this method where although the overall body of the transcripts are efficiently converted to DNA, the 5' and 3' ends are less so. Depending on the aim of the study, researchers may choose to apply or ignore this step.

Once the cDNA is synthesized it can be further fragmented to reach the desired fragment length of the sequencing system Several methods are known in the art for separating desirable cells from body fluids. Such methods include separating cells based upon buoyant density in a cell separation composition (U.S. Pat. No. 4,927,750), separating serological factors on density gradients using latex beads coated with antiserological factor (U.S. Pat. No. 3,862,303), separating cells through the use of a magnetic field (U.S. Pat. No. 4,777,145), and separating T and B cells on density gradients (U.S. Pat. No. 4,511,662). Cell separation methods known in the art may have the disadvantage of cell loss due to the sticking of cells to tubes and pipettes.

Fluorescence-activated cell sorting (FACS) is a type of flow cytometry that allows a researcher to separate samples expressing a fluorescence marker from those not expressing the marker. Cells are suspended in a stream of fluid and passing them by an electronic detection apparatus. A heterogeneous mixture of cells can be separated one cell at a time based on the light scattering and the fluorescent characteristics of each cell. The cells are suspended in a narrow, rapidly flowing stream of liquid with a large separation between cells. The stream of cells is formed into individual droplets, preferably with one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement, and the opposite charge is trapped on the droplet as it breaks from the stream. The charged droplets then fall through an electrostatic deflection system that diverts droplets into containers based upon their charge. An exemplary FACS system is illustrated in FIG. 1.

Magnet-activated cell sorting (MACS) uses superparamagnetic nanoparticles and microfluidic columns to assist in separating and isolating specific cell types and in areas like immunology, cancer research, neuroscience, and stem cell research. Cells are incubated with magnetic nanoparticles coated with antibodies against a particular surface antigen. Cells can be directly labeled or attached to the magnetic nanoparticles if the cells express the particular surface antigen and thus attach to the magnetic nanoparticles. Cells can be indirectly labeled by incubating with a primary antibody directed against a cell surface marker, with magnetic nanoparticles then binding to the primary antibody or to a molecule that is conjugated to the primary antibody.

The labeled cells in solution are then placed in a column and then a strong magnetic field is applied. During separation, the magnetically labeled cells are retained within a column. Unlabeled cells flow through. After a washing step, the column is removed from the magnetic field of the separator, and the target cells are eluted from the column. This is referred to as positive selection and can be performed by direct or indirect magnetic labeling. The type of nanoparticle can be varied for a specific antigen/molecule binding to allow for capture of different types of cells. Negative selection could alternatively be performed such that the antibody used is against surface antigen(s) which are known to be present on cells that are not of interest. After administration of the cells/magnetic nanoparticles solution onto the column the cells expressing these antigens bind to the column and fraction that goes through is collected, as it contains almost no cells with desired antigens. An exemplary set up for MACS is illustrated in FIG. 2.

The above mentioned techniques for cell separation suffer from several disadvantages, including small sample volume and throughput, preprocessing steps and duration, and cell waste (limited number of cell types can be separated from a single sample) and associated economic disadvantages.

Citation or identification of any document in this application is not an admission that such document is available as prior art to the present invention.

SUMMARY OF THE INVENTION

Accordingly, the present invention is directed to cell isolation from a heterogeneous population that obviates one or more of the problems due to limitations and disadvantages of the related art. An advantage of the present invention is to provide a method for isolating cells.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, in one embodiment, The method for isolating cells includes steps of providing a plurality of magnetic beads in a first chamber, said magnetic beads capable of binding a cell-specific binding marker so as to attach to a specific cell-type; providing cells to the first chamber, the cells including cells of the specific cell-type, such that cells of the specific cell-type bind to magnetic beads of the plurality of magnetic beads; applying a magnetic field to the first chamber and moving the magnetic field in a predetermined directions to transfer the magnetic beads to a second chamber, the second chamber in fluid communication with the first chamber; blocking fluid communication between the second chamber and the first chamber; washing the first chamber; unblocking fluid communication between the second chamber and the first chamber; removing the magnetic beads, including the magnetic beads bound to the cells of the specific cell-type, from the second chamber by applying the magnetic field to the second chamber in a second predetermined direction; and releasing the cells of the specific cell-type from the magnetic beads. Releasing the cells may include eluting.

In another aspect of the present invention, another embodiment of the cell isolation from a heterogeneous population includes providing a plurality of magnetic beads in a first chamber, said magnetic beads capable of binding to a target cell; providing cells to the first chamber, the cells including target cells, such that the target cells bind to magnetic beads of the plurality of magnetic beads; a) applying a moveable magnetic field to transfer the magnetic beads between the first chamber and a second chamber; b) blocking fluid communication between the second chamber and the first chamber; c) washing one of the first chamber and the second chamber to remove non-target cells; d) unblocking fluid communication between the second chamber and the first chamber; e) repeating steps (a)-(d) a number of times; and eluting the target cells from the magnetic beads. The number of times the steps are repeated may be predetermined or determined adaptively based on observations of the cells or beads or waste from washing.

In another aspect of the present invention, the method comprises inserting a plurality of a first target substrate in a chamber; inserting a plurality of second target substrate in the chamber; inserting a plurality of magnetic beads in the chamber; applying a moveable magnetic field to the chamber; moving the magnetic field in a first direction; moving the magnetic field in a second direction different from the first direction; and removing the magnetic beads from the chamber.

In another aspect of the present invention, another embodiment of the cell isolation from a heterogeneous population includes a) providing a plurality of magnetic beads to a plurality of respective first chambers, each respective plurality of magnetic beads provided to each first chamber containing only magnetic beads capable of binding to a respective target substrate such that each respective mixing chamber includes magnetic beads capable of binding to only one target substrate type; b) providing a sample comprising multiple target substrate types to a plurality of respective first chambers; c) applying a moveable magnetic field to transfer the magnetic beads, including any substrates bound thereto, between the first chambers and a second chambers; d) blocking fluid communication between the second chambers and the first chambers; e) washing select ones of the first chambers and the second chambers to remove non-bound substrates; f) unblocking fluid communication between the second chambers and the first chambers; g) repeating steps (c)-(f) a predetermined number of times; releasing the respective target substrates from the magnetic beads.

In another aspect of the present invention, further embodiment of a method for mixing substrates on a microfluidic platform, comprising: inserting a plurality of a first target substrate in a chamber; inserting a plurality of second target substrate in the chamber; inserting a plurality of magnetic beads in the chamber; applying a moveable magnetic field to the chamber; moving the magnetic field in a first direction; moving the magnetic field in a second direction different from the first direction; and removing the magnetic beads from the chamber.

In another aspect of the present invention, another embodiment of the a substrate-isolation platform, comprises a microfluidic chip. The microfluidic chip includes an inlet port; a plurality of first chambers connected to the inlet port by a fluid channel, the fluid channel comprising a plurality of valves; a plurality of second chambers, each of the second chambers connected to a respective first chamber by a fluid channel, each fluid channel including a controllable blocking valve; a plurality of respective outlet ports, each outlet port in fluid communication with a respective one of said second chambers and each outlet port including a blocking valve. In an embodiment of the platform, at least one of the first chambers and the second chambers are ring chambers. In an embodiment, the microfluidic chip comprises a volume of about 10 nl to about 10 μl. In an embodiment, the microfluidic chip comprises at least two layers. In a further embodiment, at least one of these layers is made of a material with high thermal conductivity such as quartz or silica to provide thermocycling on the chip. There is a magnet adjacent the microfluidic chip, wherein the relative position of the magnet with respect to the chip is variable, for example, by moving the magnet, the chip and/or the magnet field. A valve control is capable of actuating certain ones of the controllable blocking valves in response to a control signal.

A method of integrated subtype purification and RNA-Seq may be performed on the platform. For example, by providing a plurality of first magnetic beads in a first chamber, said first magnetic beads capable of binding a cell-specific marker so as to attach a specific cell-type; providing cells to the first chamber, the cells including cells of the specific cell-type, such that cells of the specific cell-type bind to the first magnetic beads; applying a magnetic field to the first chamber and moving the magnetic field in a first predetermined direction to transfer the first magnetic beads to a second chamber, the second chamber in fluid communication with the first chamber; blocking fluid communication between the second chamber and the first chamber; washing the first chamber; unblocking fluid communication between the second chamber and the first chamber; releasing the cells from the first magnetic beads; removing the first magnetic beads from the second chamber by applying a magnetic field from the second chamber in a second predetermined direction; blocking fluid communication between the second chamber and the first chamber; lysing the cells; capturing target substrates from the lysed cells using second magnetic beads; applying a magnetic field to the second chamber and moving the magnetic field in a third predetermined direction to transfer the target substrates captured by the second magnetic beads to the first chamber; mixing the second magnetic beads and the captured target substrates with mRNA-seq reagents; cycling through a range of temperatures to create a PCR product; and applying solid phase reversible immobilization (SPRI) beads to the PCR product to clean up DNA.

In an embodiment, the method for isolating a target substrate wherein the second magnetic beads are oligo (dT) beads. In an embodiment, the method for isolating a target substrate wherein the second magnetic beads are Solid Phase Reversible Immobilization beads. In an embodiment, the method for isolating a target substrate wherein the DNA-binding beads are charge switch silica beads. In an embodiment, the method for isolating a target substrate wherein the DNA-binding beads are solid phase reversible immobilization (SPRI) beads. In an embodiment, the method for isolating a target substrate wherein the DNA-binding beads are dsDNA antibodies. In an embodiment, the method for isolating a target substrate wherein the target substrates are RNA. In an embodiment, the method for isolating a target substrate wherein the cycling ranges from about 5 cycles to about 10 cycles. In a further embodiment of the method, the cycling ranges from about 10 cycles to about 90 cycles. In an embodiment of the method, the cycling ranges from about 5 cycles to about 90 cycles. In a further embodiment of the method, the cycling ranges from about 10 cycles to about 80 cycles. In an embodiment of the method, the cycling ranges from about 10 cycles to about 70 cycles. In a further embodiment of the method, the cycling ranges from about 10 cycles to about 60 cycles. In an embodiment of the method, the cycling ranges from about 10 cycles to about 50 cycles. In a further embodiment of the method, the cycling ranges from about 10 cycles to about 40 cycles. In an embodiment of the method, the cycling ranges from about 10 cycles to about 30 cycles.

In an aspect, the invention provides a kit comprising an integrated subtype purification and RNA-Seq on a platform comprising a microfluidic chip, comprising a plurality of processing units, each processing unit comprising: an inlet port, a plurality of first chambers connected to the inlet port by a fluid channel, the fluid channel comprising a plurality of valves, a plurality of second chambers, each of the second chambers connected to a respective first chamber by a fluid channel, each fluid channel including a controllable blocking valve, and a plurality of respective outlet ports, each outlet port in fluid communication with a respective one of said second chambers and each outlet port including a blocking valve; and a movable magnet adjacent the microfluidic chip, the method comprising: providing a plurality of first magnetic beads in a first chamber, said first magnetic beads capable of binding a cell-specific marker so as to attach a specific cell-type; providing cells to the first chamber, the cells including cells of the specific cell-type, such that cells of the specific cell-type bind to the first magnetic beads; applying a magnetic field to the first chamber and moving the magnetic field in a first predetermined direction to transfer the first magnetic beads to a second chamber, the second chamber in fluid communication with the first chamber; blocking fluid communication between the second chamber and the first chamber; washing the first chamber; unblocking fluid communication between the second chamber and the first chamber; releasing the cells from the first magnetic beads; removing the first magnetic beads from the second chamber by applying a magnetic field from the second chamber in a second predetermined direction; blocking fluid communication between the second chamber and the first chamber; lysing the cells in the second chamber; capturing target substrates from the lysed cells using dynamically altered magnetic beads; applying a magnetic field to the second chamber and moving the magnetic field in a third predetermined direction to transfer the target substrates captured by the dynamically altered magnetic beads to the first chamber; mixing the dynamically altered magnetic beads and the captured target substrates with mRNA-seq reagents; cycling through a range of temperatures to create a PCR product; and applying DNA-binding beads to the PCR product to clean up DNA. In an embodiment, the kit further comprises magnetic beads in a first chamber comprises the first magnetic beads conjugated to an antibody wherein the first magnetic beads are capable of binding a cell-specific marker so as to attach a specific cell-type. In a further embodiment, the kit comprises an antibody and cell-specific marker which are enzymatically cleaved.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as “comprises”, “comprised”, “comprising” and the like can have the meaning attributed to it in U.S. Patent law; e.g., they can mean “includes”, “included”, “including”, and the like; and that terms such as “consisting essentially of” and “consists essentially of” have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1A:
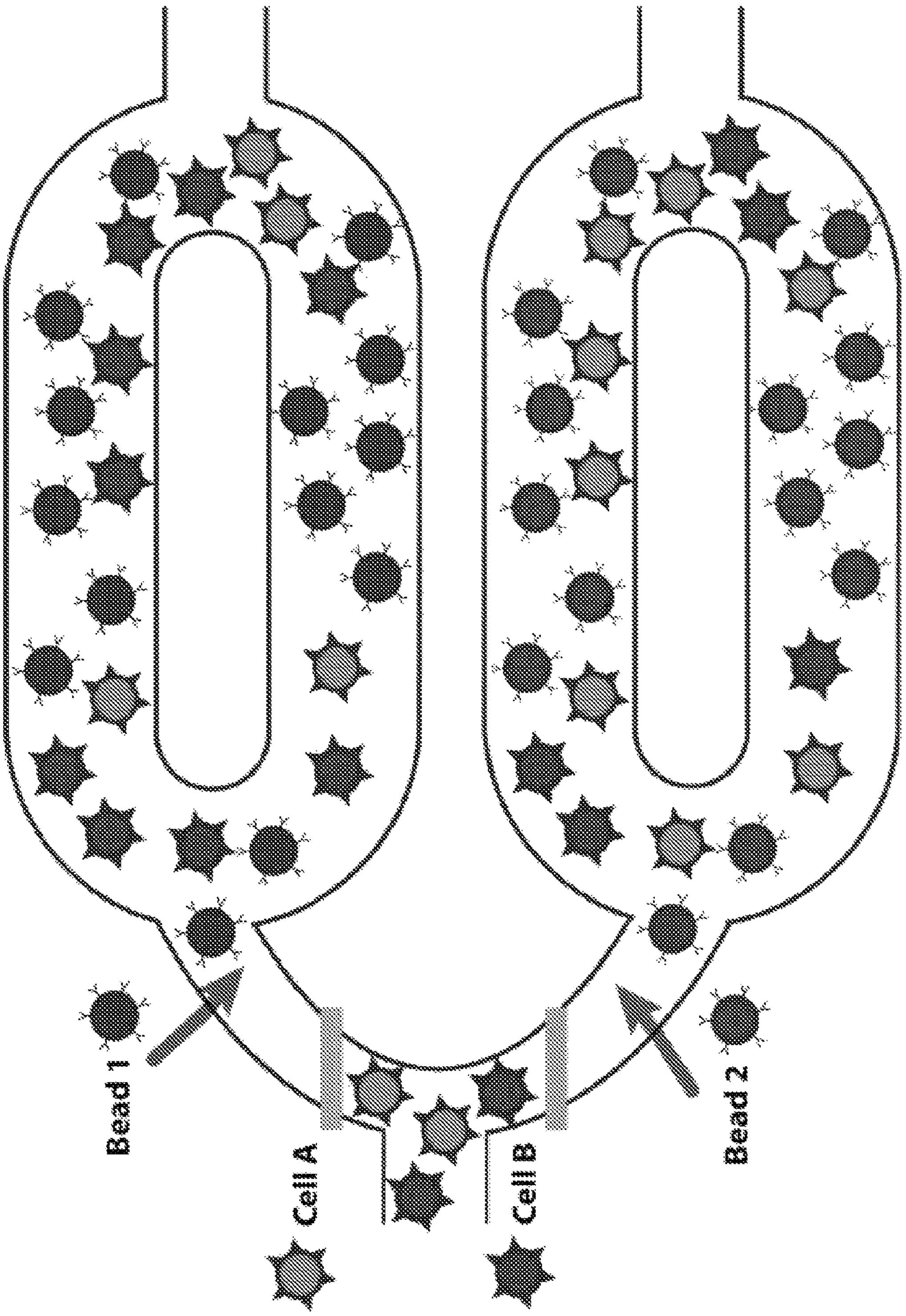
FIG. 1A is an illustration of an exemplary microfluidic mechanism for sorting cells according to principles of the present invention.

The present disclosure provides an apparatus and method for the sorting of biological material that does not involve a column and is intended to improve throughput and speed of the sorting process. Inventors of the present invention began with an overall goal to develop a system for cellular profiling of multiple cell populations in hundreds (or thousands) of Systemic Lupus Erythematosus ("SLE") patients, although the present techniques are not intended to be limited to these specific cell types. Inventors identified a need for more effective means of profiling cell subtypes from blood in order to gain understanding of numerous immune-related disorders. Autoimmune disorders are generally characterized by: autoantibodies and immune complex deposition in tissues, unclear disease mechanisms, likely involvement of B cells, also pDCs, neutrophils, and CD4 T cells; and cells from SLE patients show elevated IFN response signatures.

To achieve the prescribed goals, the inventor strived to overcome known challenges such as small sample volumes (e.g. single cells), unpredictable flow and adhesion characteristics, and difficulty in isolating rare cells effectively and reproducibly, and goals of manageable costs and point of care use. Characteristics of the present invention lend themselves to portability, automation ability, rare cell isolation, reduced sample preprocessing and time, reduced costs over prior techniques, integration with an RNA-seq Platform, described in International Patent Application No. PCT/US2015/049178, which is incorporated by reference in its entirety as if fully set forth herein, and simultaneous processing of multiple samples for a reduction in analysis time. A non-limiting, illustrative example of advantages of microfluidic cell sorting according to principles of the present invention versus Fluorescence-Activated Cell Sorting (FACS) is provided by the following Table.

| | FACS | Microfluidics |
|---|---|---|
| Hands On Time | 3 hours | 20 min |
| Time for Isolation | 2 hours | 30 min |
| Number of Markers per Run | 4 | >6 |
| Sample Processing Time | 10 mins/sample | 1 hr/experiment |
| Capital Equipment Cost | $500K | $5K |
| Yield | | 3% |

FACS cost is approximately $75/hour with 10 patients per experiment and 12 markers per experiment. In sum, as the cost of sequencing has dropped, the cost of sample preparation has increased such that now more than 50% of the total cost is related to sample preparation.

As just one example, to sequence a transcriptome or other RNA, cells must be lysed and the nucleic acid purified, fragmented, tagged with adaptors, and size-selected before loading on a sequencing instrument. These steps demand significant application of resources including reagents, other consumables, labor, and possibly automation equipment (to mitigate labor costs) that ultimately limit throughput. To eliminate the sample preparation "bottleneck" one needs to be able to develop a fully-integrated workflow (to minimize labor costs), micro-scale automation, and high-throughput device to match NGS capacity (reusable devices for the lowest cost applications). One aspect which has been missing in the art is on-chip filtration. The present invention provides a novel method to move the reagents and products back and forth to accomplish on-chip filtration. To enable this method, several things need to be accomplished: (1) combine samples and reagents in precise ratios (2) mix samples and reagents and (3) trap and wash particulates, i.e., a method or way to handle solids.

Applicants endeavored and demonstrated that it was possible to automate the entire workflow, including the material, into one system. Automation into one system provided the ability to minimize the loss of sample and material over the course of the workflow. To this end, Applicants provide a novel device and method enabling one to start with smaller amounts of sample and therefore increasing the application of sequencing to systems where sample amount was an obstacle.

As discussed herein, cell subset-specific signatures are clinically informative. If one examines the gene expression profile in a particular subclass of T cells, for example, in case-control studies, a wide array of applications are enabled: the subset of cells involved in disease can be identified, the genes and gene products involved in disease can be identified, the gene expression signature can be used to assist in predicting the course of the disease or to monitor drug studies, the patient classes that respond to therapy (e.g., marketed drugs) can be identified or predicted. As just one example, in one aspect of the invention, autoimmune diseases are poorly understood and treatments for such diseases would benefit from identifying which proteins would make good drug targets. A $CD8^+$ T cell transcription signature predicts prognosis in a given autoimmune disease (McKinney, E. F; Lyons, P. A., Carr, E. J.; Hollis, J. L.; Jayne, D. R. W.; Willcocks, L. C.; Koukoulaki, M.; Brazma, A.; Jovanovic, V.; Kemeny, D. M.; Pllard, A. J. MacAry, P. A.; Chaudhry, A. N.; Smith, K. G. C. *Nat. Med.* 2010, 16, 586-591). Therefore, there is a need to find these transcription signatures in order to stratify these patients and identify cell subset-specific signatures. Immune cell subset-specific analyses are needed in order to identify autoimmune disease, tumor immunity, and host responses during infection. Many immune system disorders or dysfunction are related to rare immune subset cells (>20) that regulate it, these rare immune cells are of interest. The conventional FACS method for subset specific analysis is impractical for many samples. The present system described herein solves this problem by integrating multiplex cell subset purification (affinity) and RNA-Seq sample preparation for scalable subset-specific gene expression profiling. Applicants herein address how to examine this relationship in a highly specific way and provide therapeutics accordingly.

FIG. 1A illustrates an exemplary microfluidic mechanism for sorting cells according to principles of the present invention. As illustrated in FIG. 1A, different cell types, Cells A and Cells B (illustrated as "star-like" particles), are inputted to a microfluidic device having at least one microfluidic mixing chamber. The shape of the mixing vessel or chamber may be a ring or may be any other shape (which may or may not comprise the topology of a ring, linked rings, or fused rings) as would be appropriate for the proper functioning of the system, as described below. For the purposes of illustration, without limitation, a ring is shown in the figures. As illustrated, two mixing rings may be connected to a common channel for insertion of cells to each of the rings. In the system, the types of cell inputted to each ring are not limited. For example, all cell types in a sample may be allowed to enter any of the mixing rings. It is envisioned by the inventors that the system will include a mixing ring corresponding to each type of cell to be collected by the system, although this is not required. The system further includes a means for blocking the common channel to prevent entry of the sample into the mixing well. The means for blocking the common channel may be a pressure- or vacuum-actuated valve or other suitable means for blocking a microfluidic channel including mechanical, thermal, electrical, or optical actuation. The means for blocking may be capable of fully or partially blocking flow within the channel. In other words, the means for blocking may serve as a filter or sieve valve or a full valve, as may be appreciated in accordance with principles of this disclosure. An example of such valves may be found in International Patent Application Publication No. WO 2015/050998. Although not illustrated, the chambers may be divided or subdivided into multiple subchambers sufficient for mixing up to 10 components in pre-defined ratios.

According to an aspect of the present invention, magnetic nanoparticles ("magnetic beads") (illustrated as circular particles) are introduced into each mixing ring, such that each mixing ring includes a single type of magnetic nanoparticle or bead that attaches or binds to a single type of cell in the sample, as may be appreciated by one of skill in the art. The magnetic beads may be introduced into the mixing ring or circuit before introduction of the sample into the mixing ring or after introduction of the sample into the mixing ring.

Figure 1B:
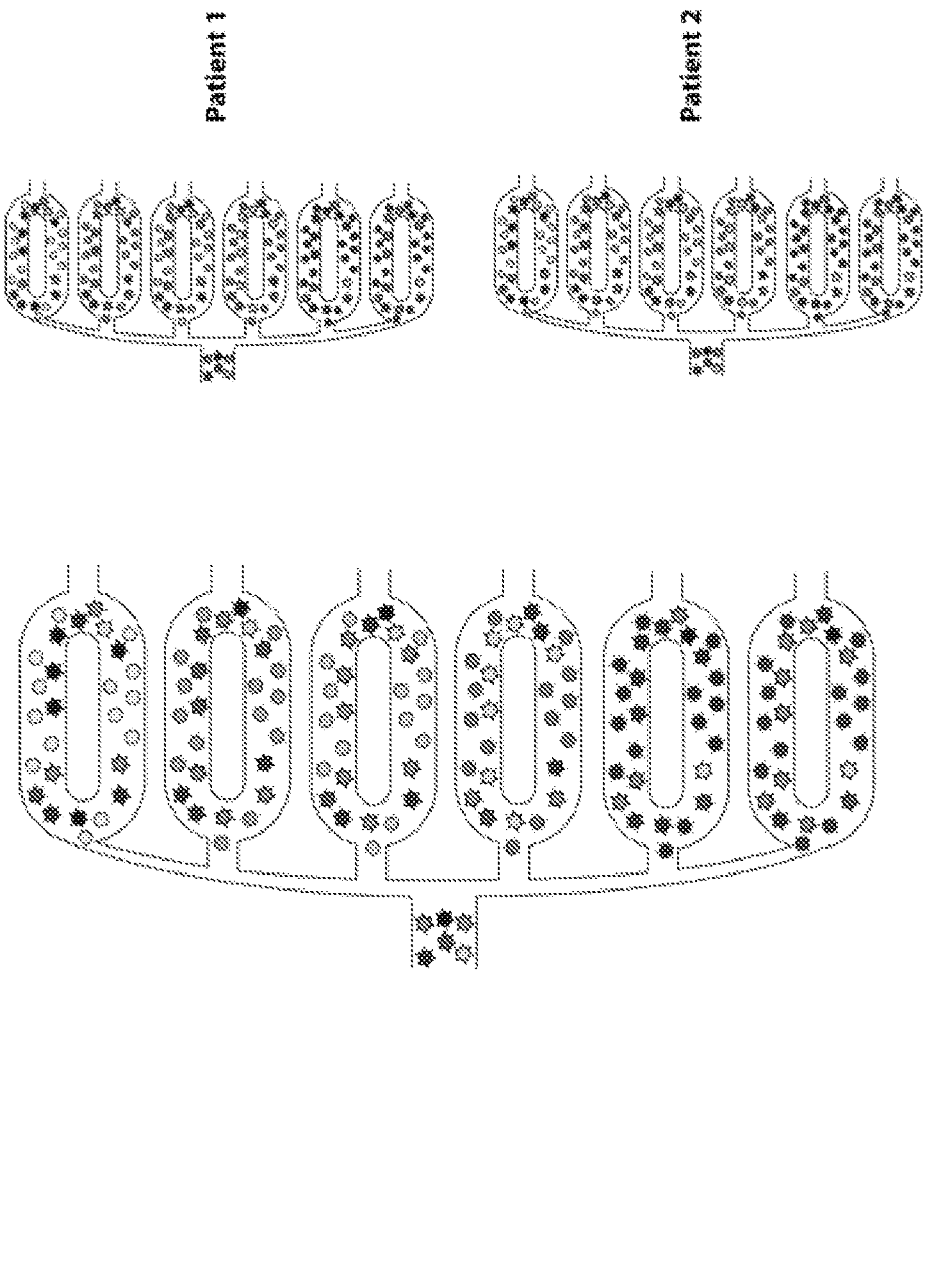
FIG. 1B illustrates a system according to the principles of the present invention.
Figure 2:
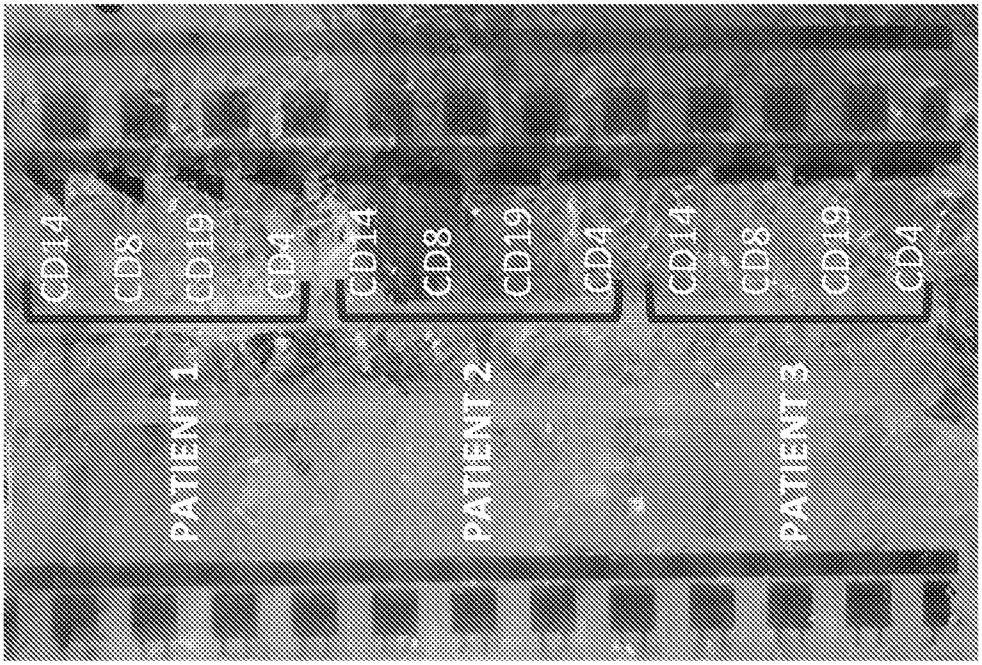
FIG. 2 is a photograph of a physical embodiment of the present invention.

FIG. 1B illustrates a system according to the principles of the present invention including a plurality of mixing chambers or rings, each including a different bead for binding to a particular cell type. As also illustrated in FIG. 1B, each patient sample may be introduced into a separate grouping of mixing rings with the appropriate bead type.

An example of cell sorting according to principles of the present invention is illustrated with the aid of FIG. 3. As illustrated in FIG. 3A, a plurality of magnetic beads (Bead 1) are provided in a first mixing chamber. The magnetic beads are capable of binding a cell-specific binding marker so as to attach to a specific cell-type. As illustrated, a plurality of magnetic beads (Bead 2) capable of binding a different cell-specific binding marker may be provided to a second mixing chamber if a second type of cells is to be sorted.

Figure 3A:
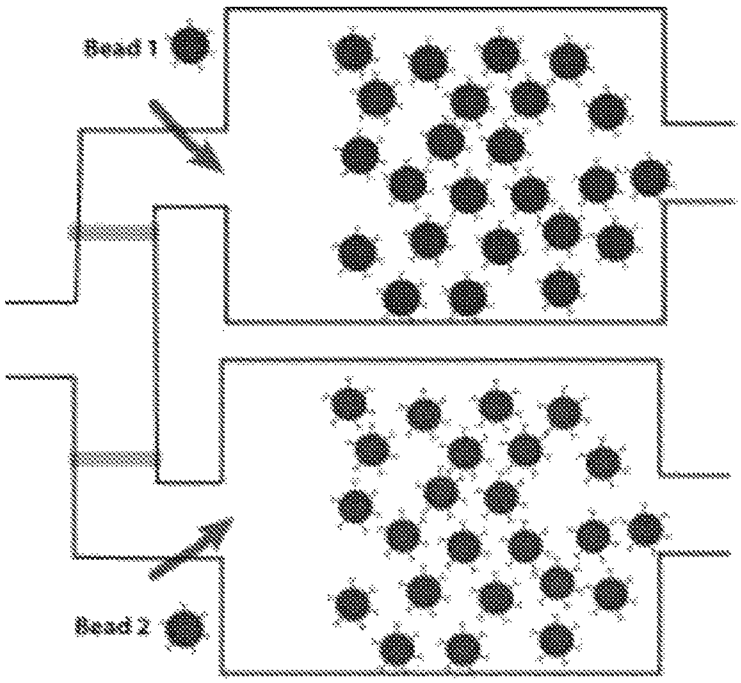
FIGS. 3A-3D illustrate an example of cell sorting according to principles of the present invention.
Figure 3B:
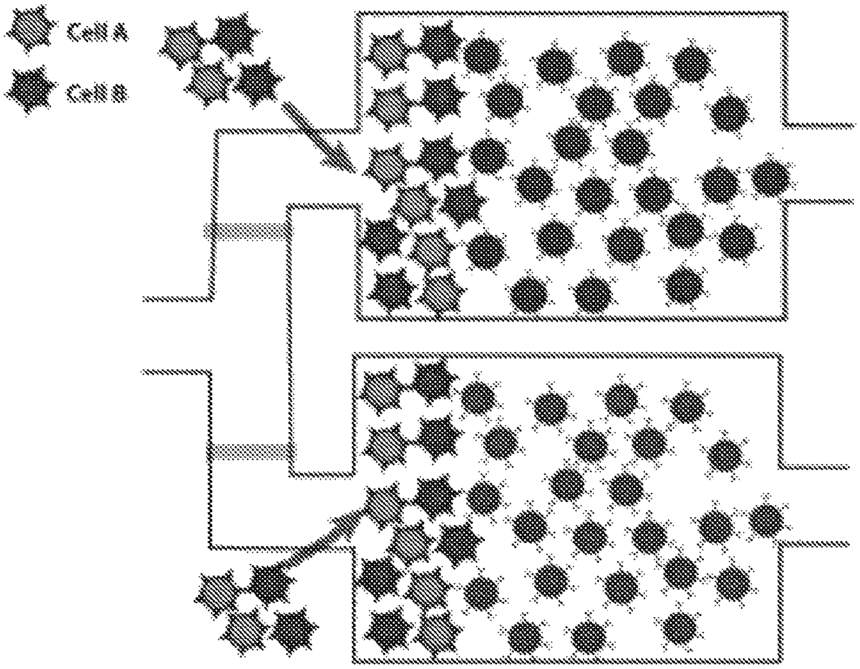

As illustrated in FIG. 3B, cells are then provided to the mixing chamber, the cells including cells of the specific cell-type, such that cells of the specific cell-type bind to magnetic beads of the plurality of magnetic beads in the first mixing chamber. If there is a second mixing chamber, then cells from the same sample may be provided to the second mixing chamber, such that cells of a different specific cell-type within the sample bind to the magnetic beads within the second mixing chamber.

Figure 3C:
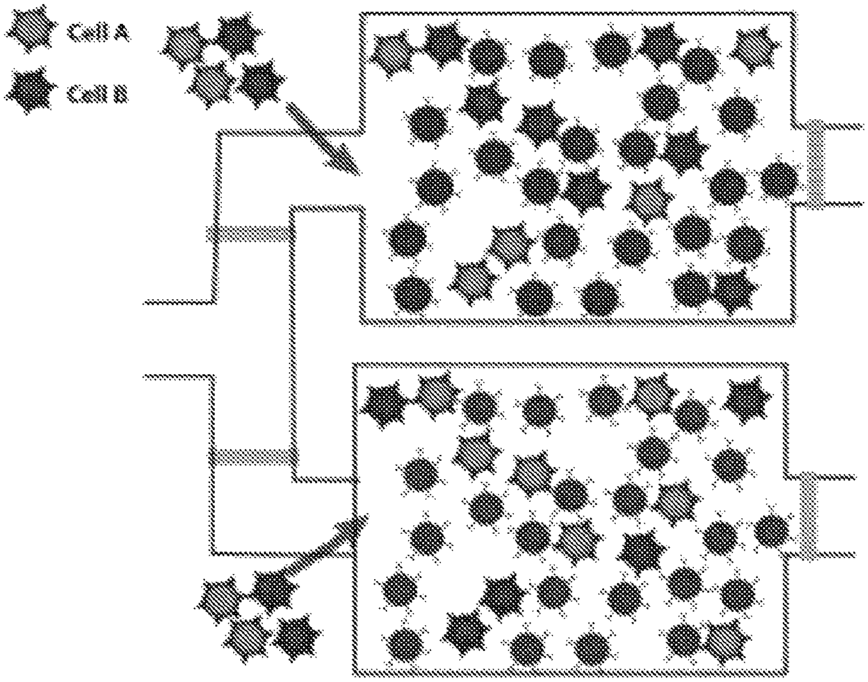
Figure 3D:
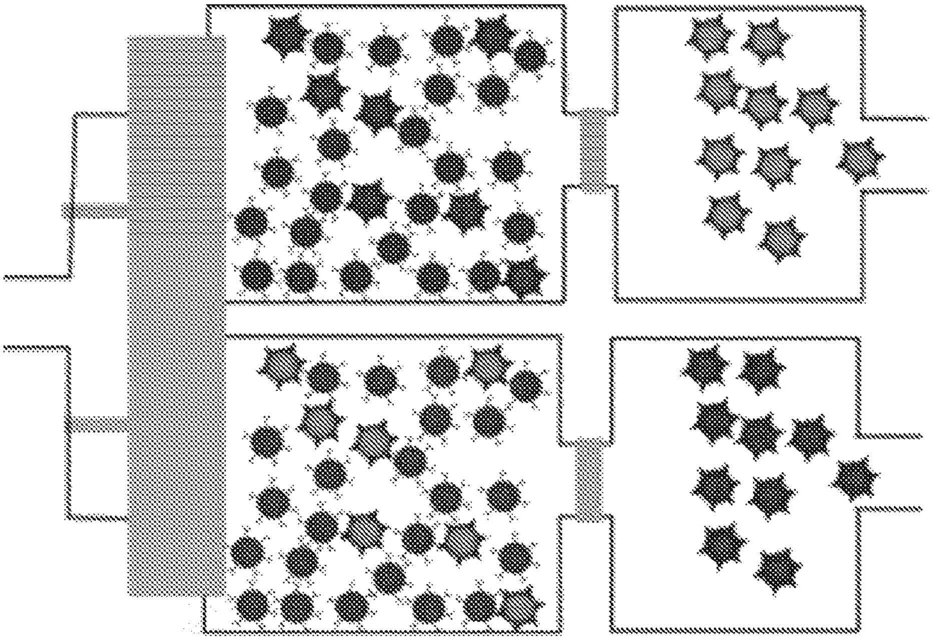
Figure 4:
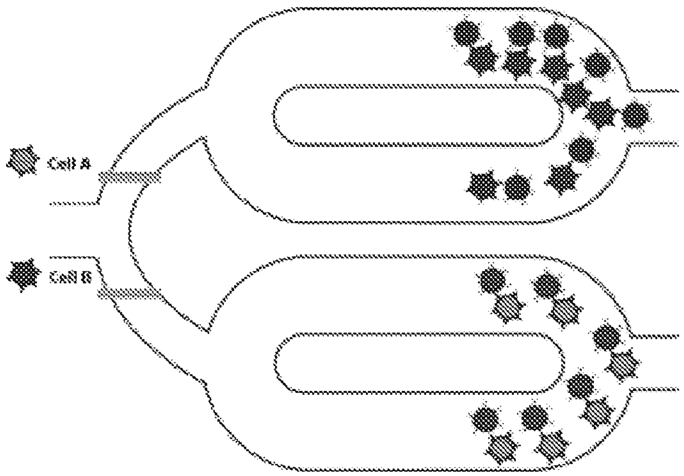
FIG. 4 illustrates removal of magnetic beads from a system according to principles of the present invention.

A magnetic field is applied to the first mixing chamber. The magnetic field may be applied, for example, by bringing a permanent magnet, such as a Neodynium magnet, or an electro-magnet, into proximity of the first mixing chamber. The magnetic field is moved in a predetermined direction to transfer the magnetic beads to a first holding chamber, the first holding chamber in fluid communication with the first mixing chamber. If there is a second mixing chamber, the same magnetic field may be applied to the second mixing chamber. The magnetic field may be applied to both the first mixing chamber and the second mixing chamber at the same time to move or hold the beads in mixing or the holding chamber. Then, fluid communication is blocked between the holding chamber(s) and the mixing chamber(s). If the beads have been moved to the holding chamber, the mixing chamber(s) is washed and then fluid communication between the holding chamber and the mixing chamber is then unblocked. The magnetic beads are then removed from the holding chamber, including the magnetic beads bound to the cells of the specific cell-type, by applying the magnetic field to the holding chamber in a second predetermined direction. These steps are illustrated in FIGS. 3C-D. For example, the magnetic beads in the holding chamber may be removed from the system (FIG. 4) or may be moved back to the mixing chamber after all other unbound cells have been washed from the mixing chamber. Then, the cells of the specific cell-type may then be released from the magnetic beads, while keeping these newly sorted cells separate from other cell types. For example, the cells of the specific cell-type may be released from the magnetic beads by eluting. The cells may then be lysed and RNA isolated.

Instead of removing the specific cell-type from system and releasing them from the magnetic beads, the specific cell-type still bound to the magnetic beads may be moved back to the mixing chamber. Then, fluid communication between the mixing chamber and the holding chamber may be blocked. Then, the holding chamber may be washed prior to releasing the cells of the specific cell-type from the magnetic beads. This additional movement ("pass") of the specific cell-type bound to the magnetic beads allows for further purification of the sample to remove additional cells or materials not of interest. Such passes may be repeated to reach desired purification of the sample by passing the cells from chamber to chamber, blocking fluid communication between the chambers, washing the chamber not holding the specific cell-type bound to the magnetic beads, unblocking fluid communication between the chambers and then passing the sample back to the washed chamber.

Figure 5:
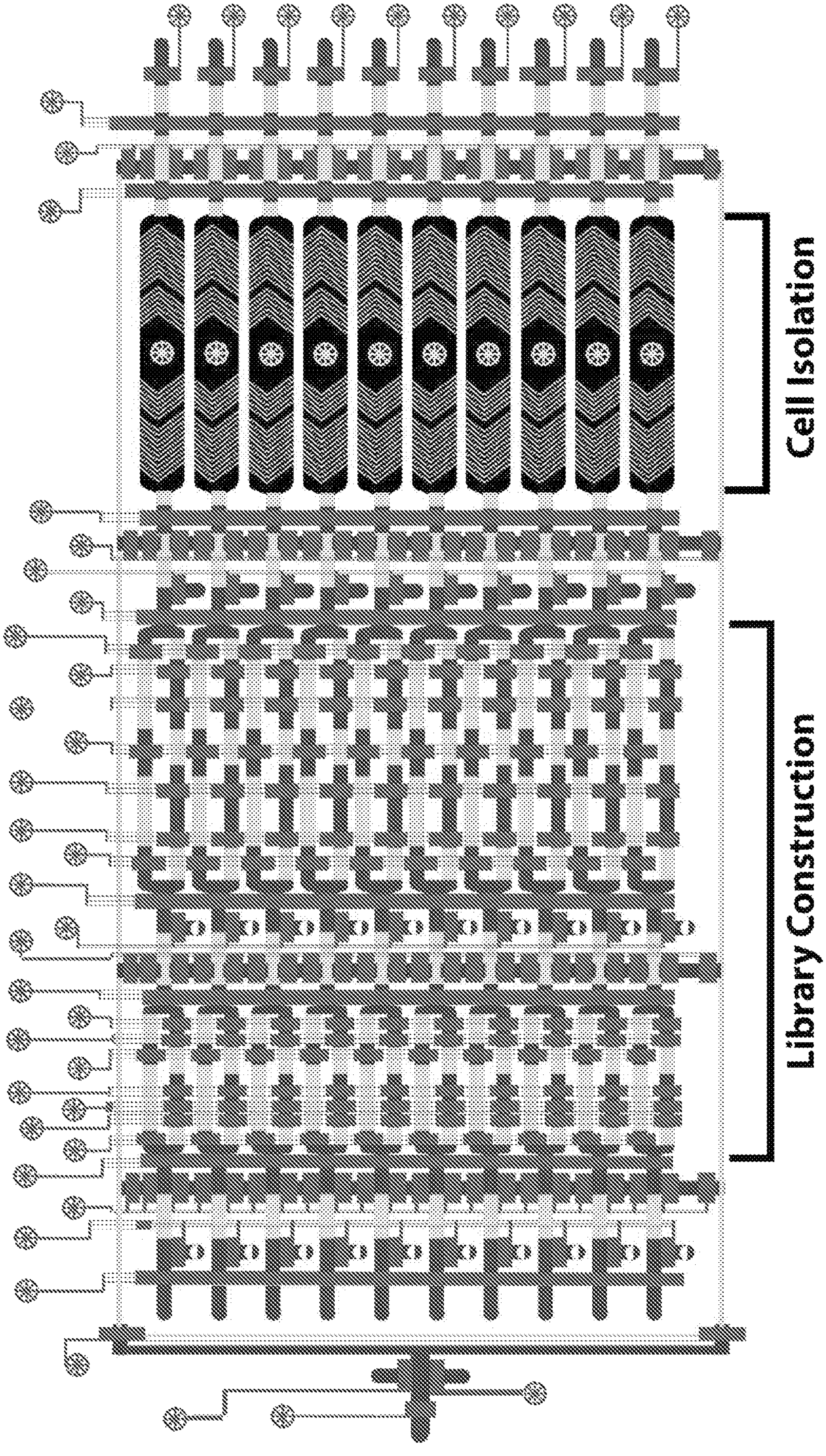
FIG. 5 is a schematic illustration of a system according to principles of the present invention.

FIG. 5 is a schematic illustration of a system according to principles of the present invention, including mixing chambers and holding chambers for sorting or isolating multiple cell or target substrate types. An exemplary embodiment of the present invention includes a microfluidic chip. The microfluidic chip includes an inlet port. A plurality of first chambers are connected to the inlet port by a fluid channel. The fluid channel includes a plurality of valves. The microfluidic chip further includes a plurality of second chambers. Each of the second chambers is connected to a respective first chamber by a fluid channel. Each of the fluid channels connecting a respective first chamber and a respective second chamber includes a controllable blocking valve. Each of a plurality of respective outlet ports is in fluid communication with a respective one of the second chambers. Each outlet port includes a blocking valve. There is a movable magnet adjacent the microfluidic chip and a valve control capable of actuating certain ones of the controllable blocking valves in response to a control signal. The system of the present invention is not limited to a microfluidic chip or a microfluidic scale, and may comprise a plurality of chambers without chip-level integration.

Figure 6:
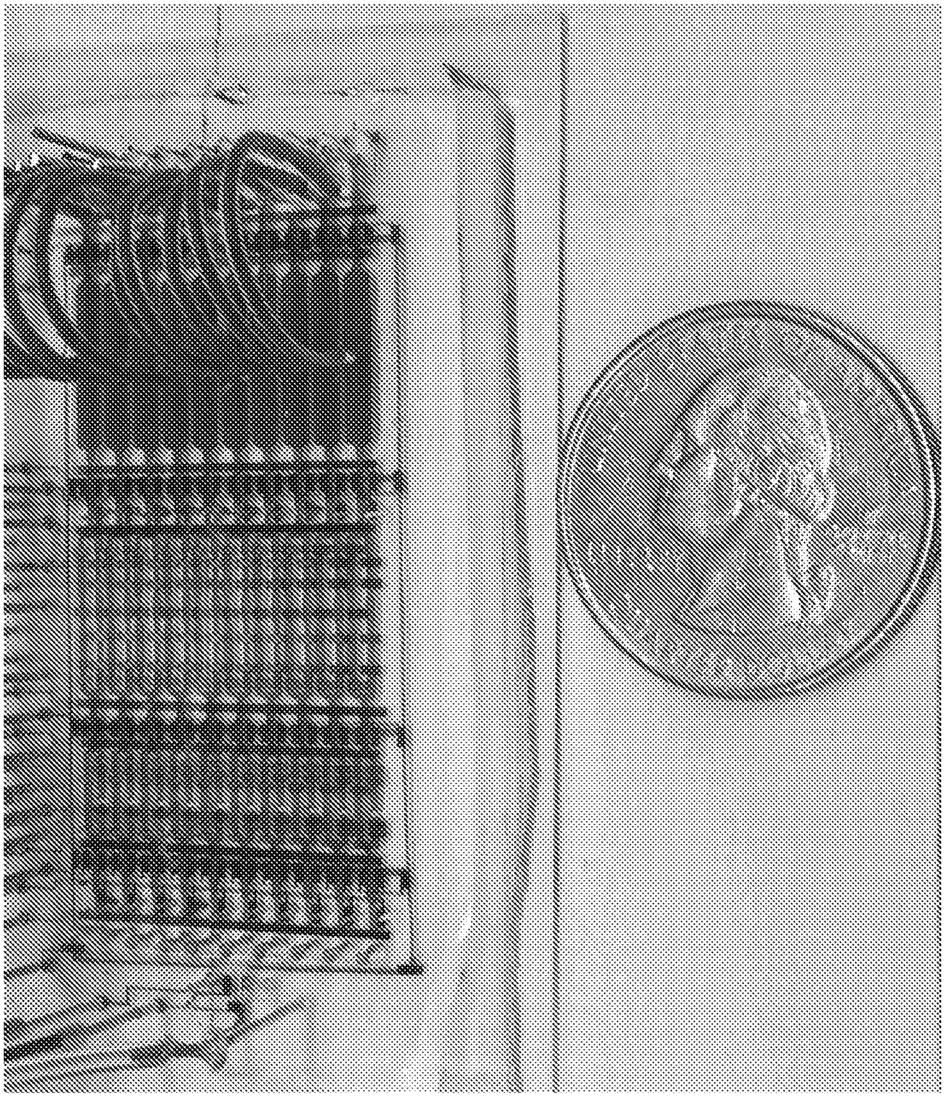
FIG. 6 is a photograph of a physical embodiment of the present invention.
Figure 7A:
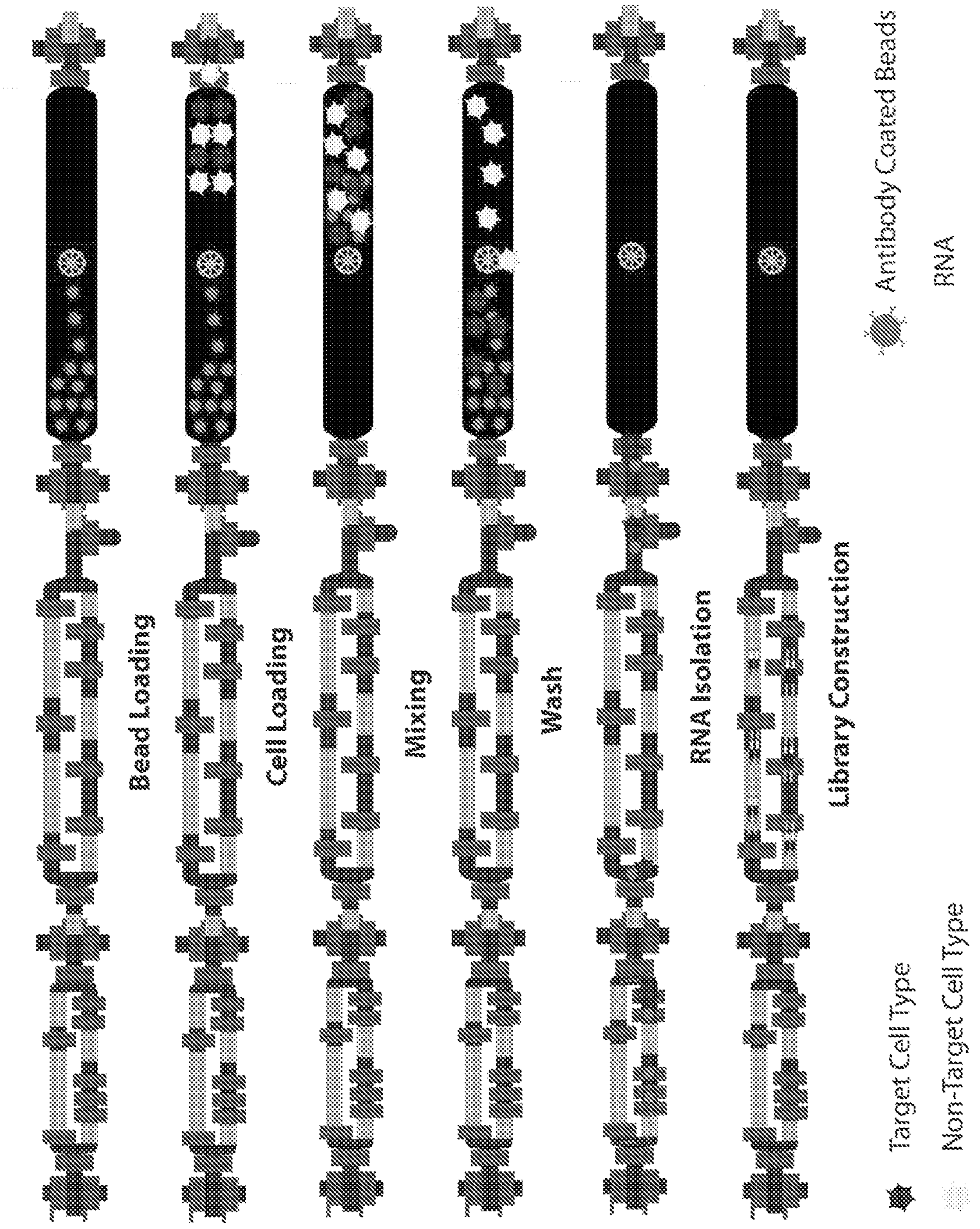
FIGS. 7A-7B illustrates operation and embodiments of the present invention.
Figure 7B:
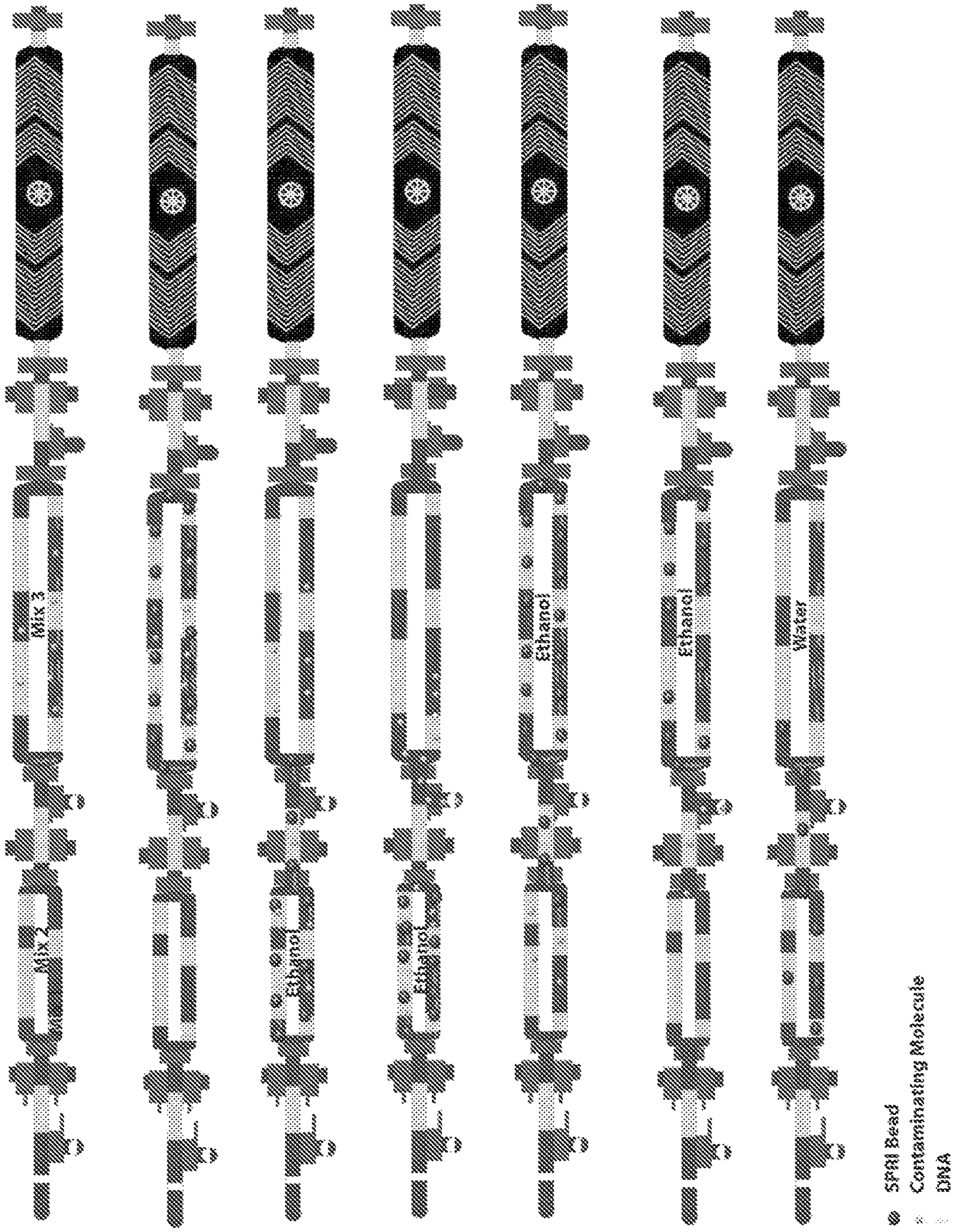

FIG. 6 is a photograph of a physical embodiment of the present invention with an American quarter to illustrate scale. FIGS. 7 A-B illustrates operation and embodiments of the present invention.

Figure 8:
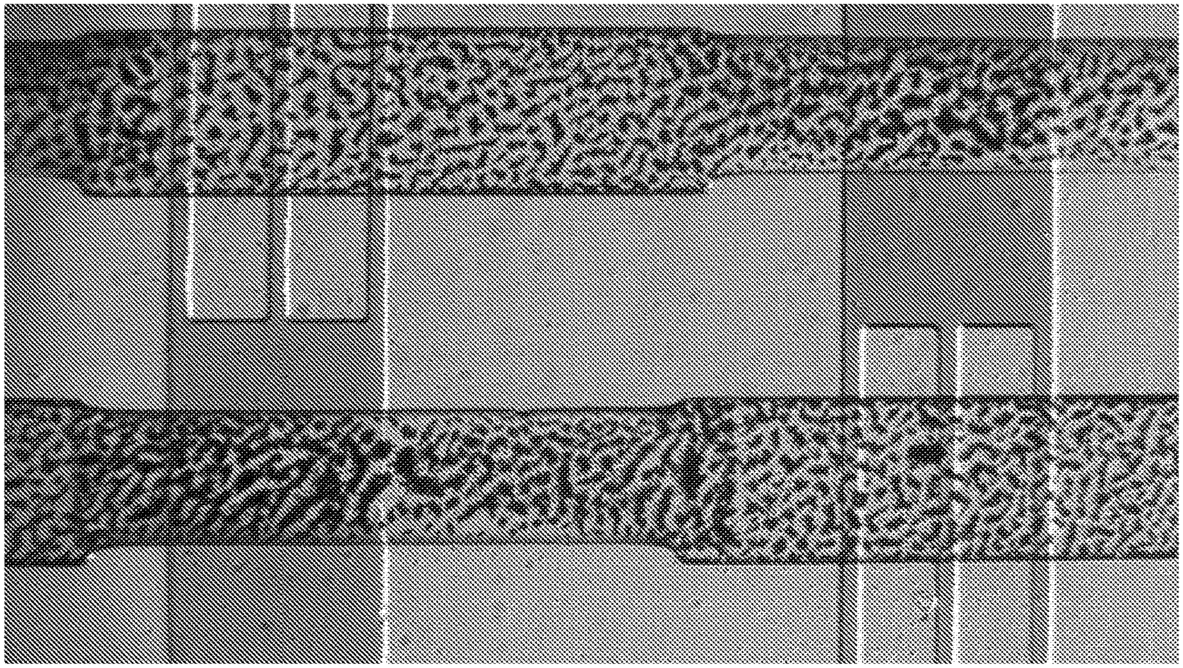
FIG. 8 shows a washing step in an experiment according to principles of the present invention.
Figure 9:
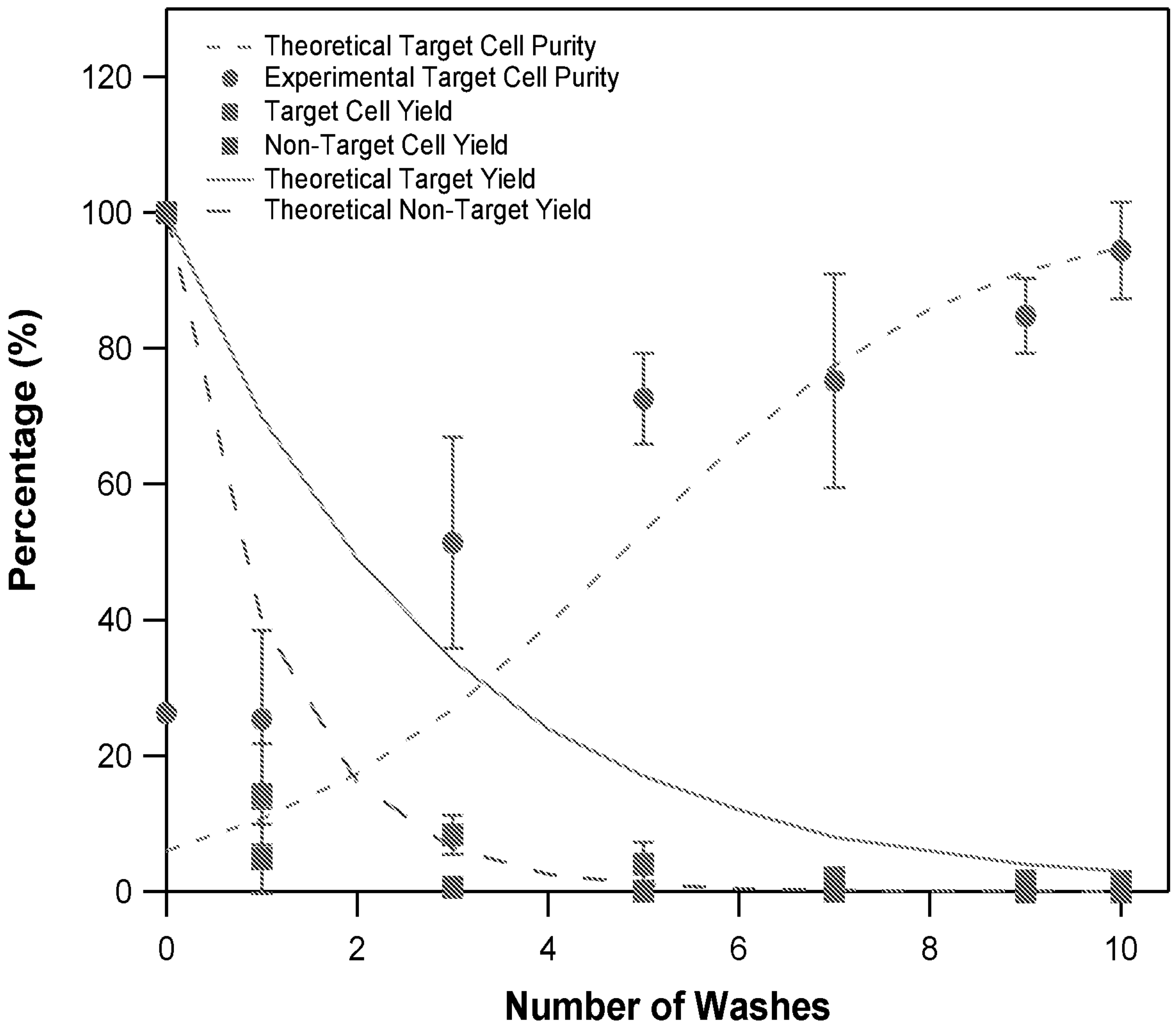
FIG. 9 is a graph showing the experimental results of sample purity after a number of washes or passes.
Figure 10:
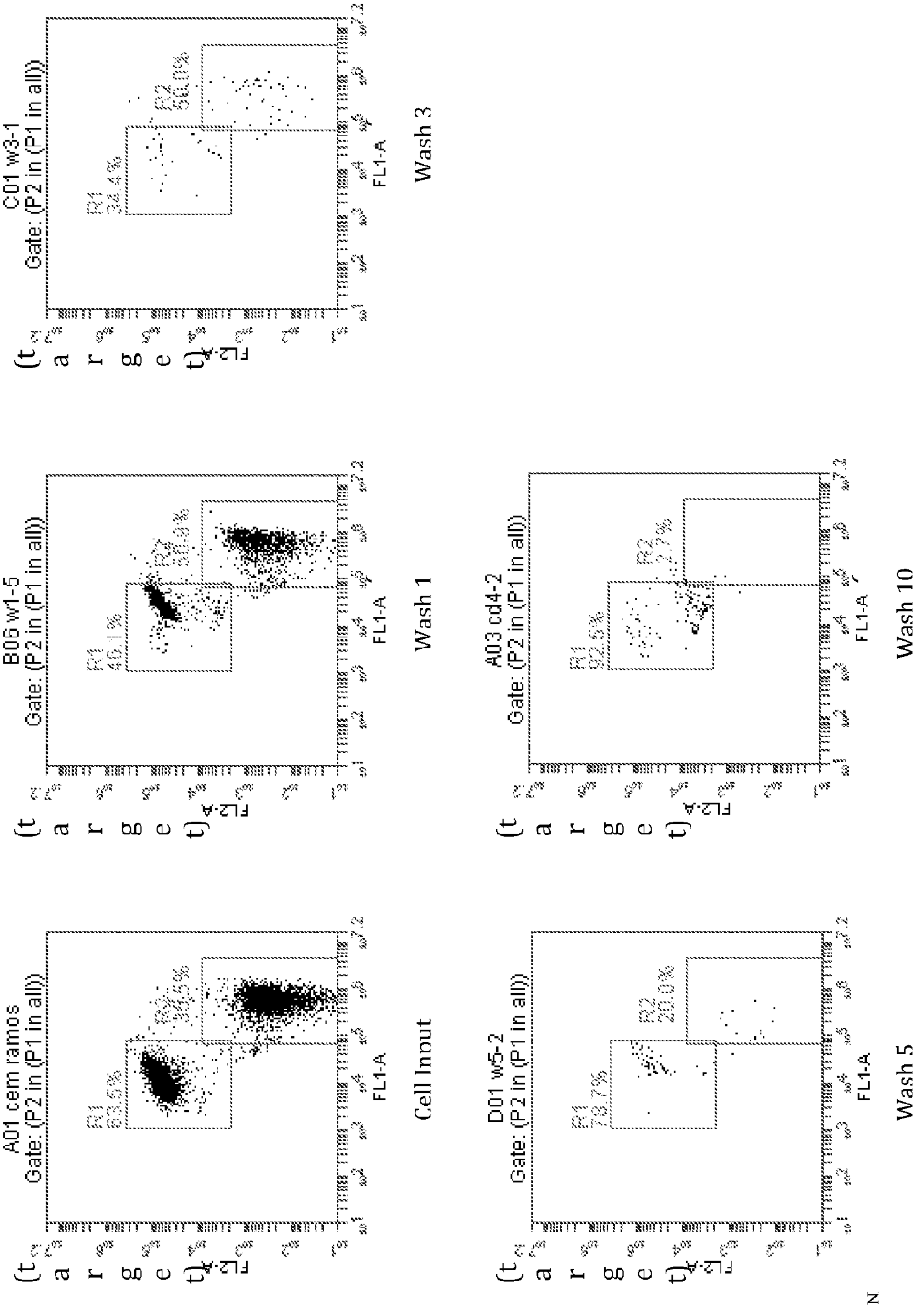
FIGS. 10 and 11 further illustrate experimental data based on the number of washes or passes according to principles of the present invention.
Figure 11:
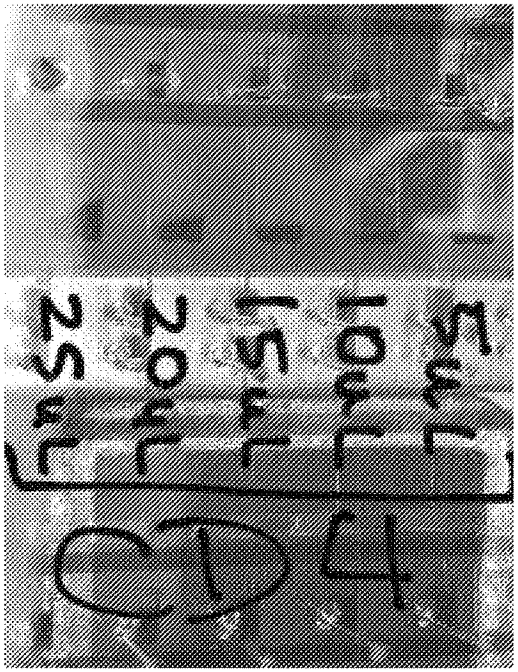
Figure 11:
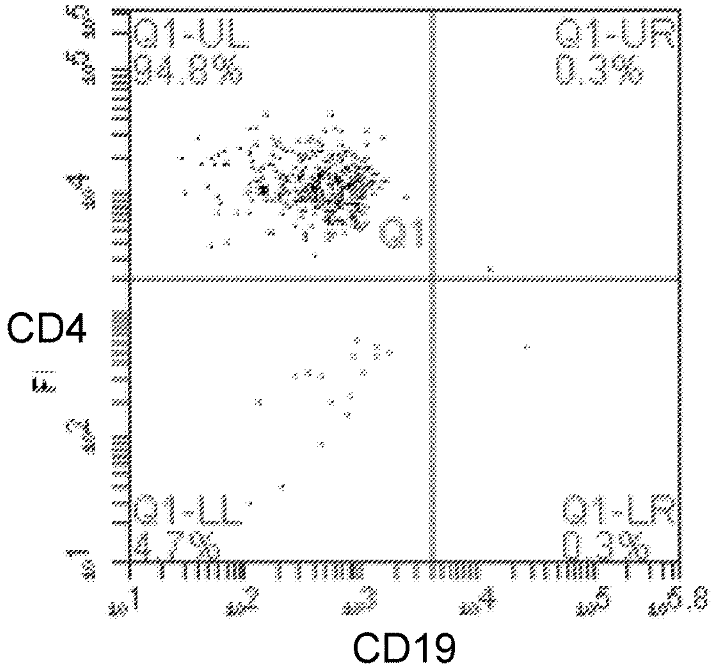
Figure 12A:
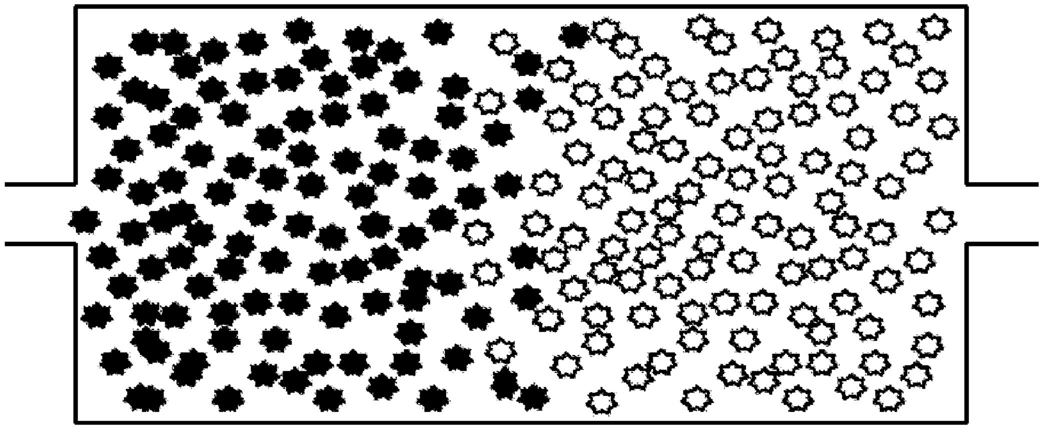
FIGS. 12A-12I illustrates additional uses of chambers according to principles of the present invention.
Figure 12B:
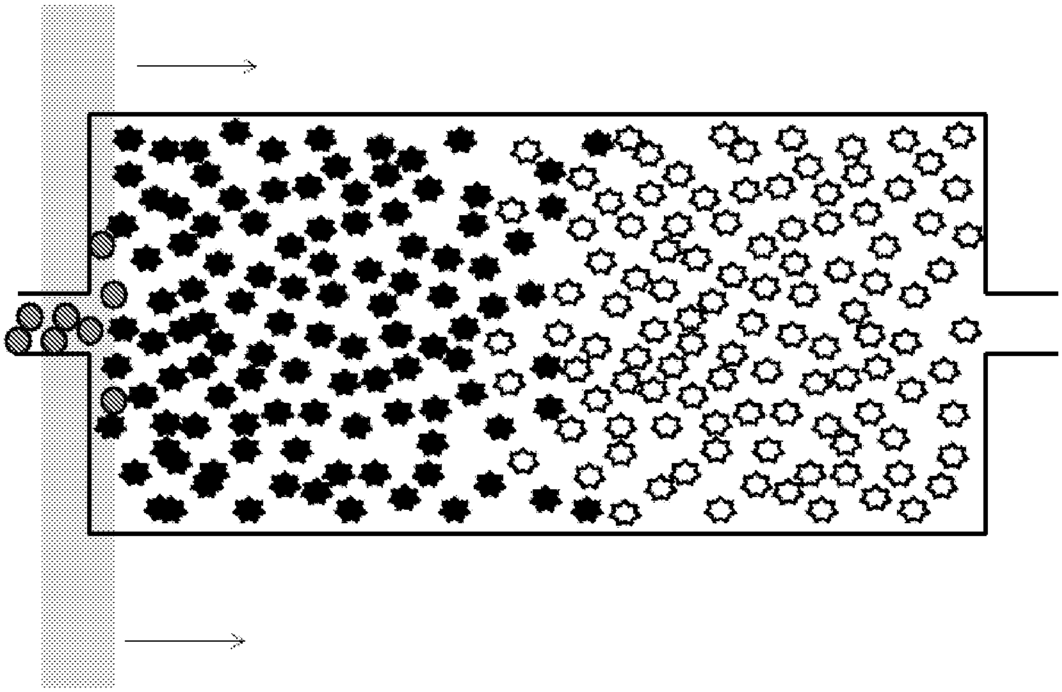
Figure 12C:
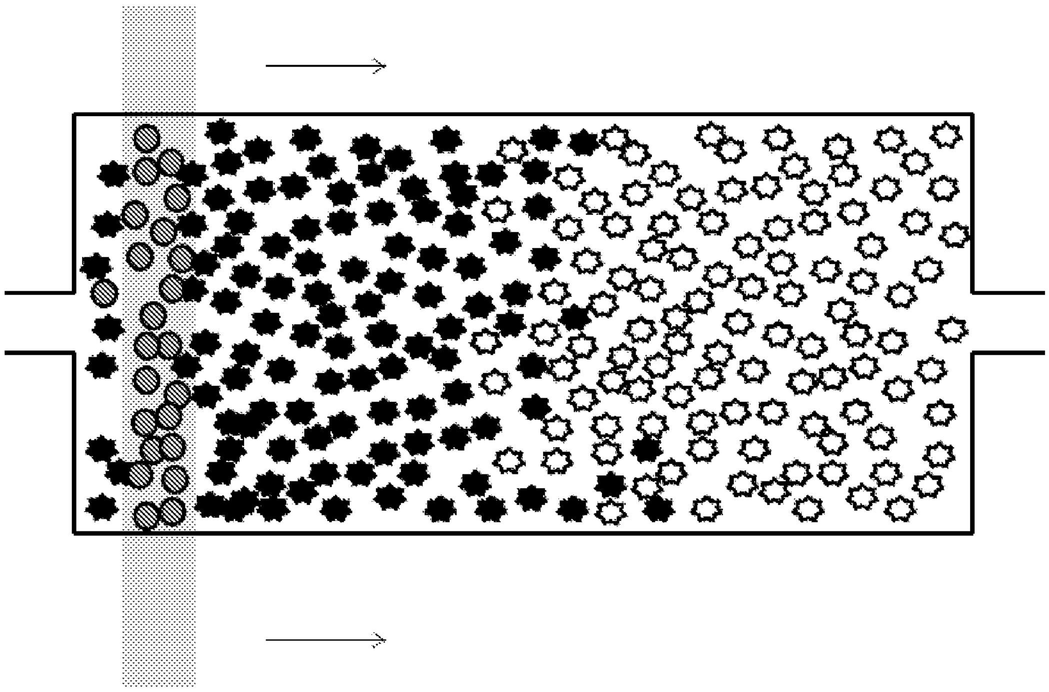
Figure 12D:
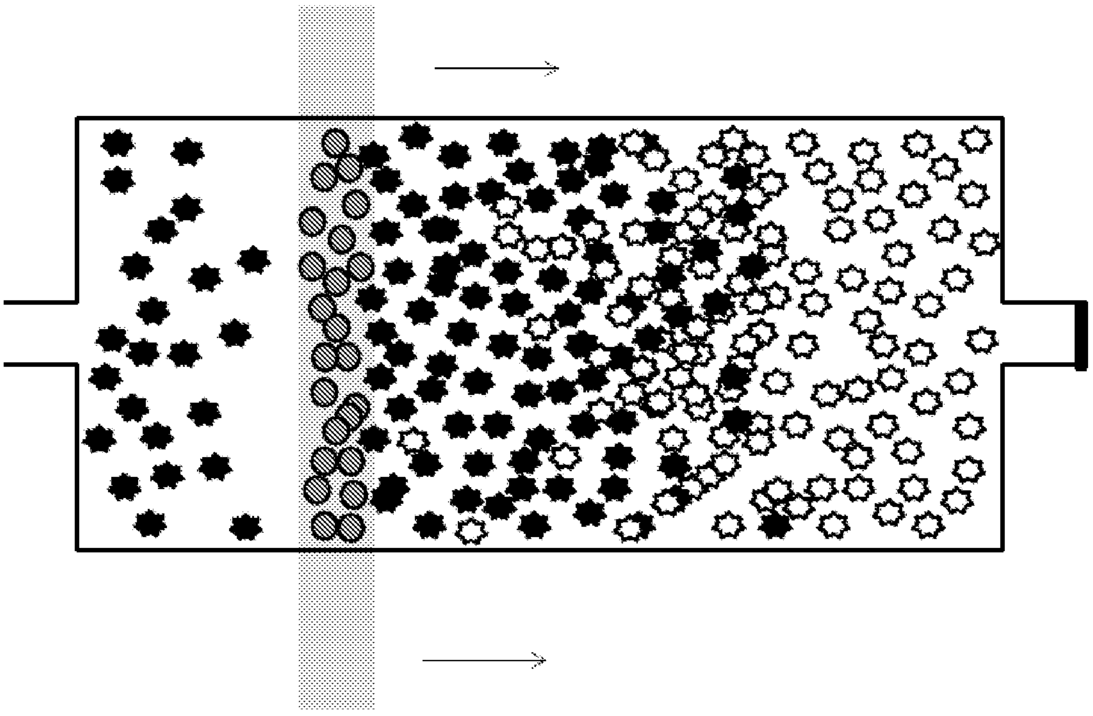
Figure 12E:
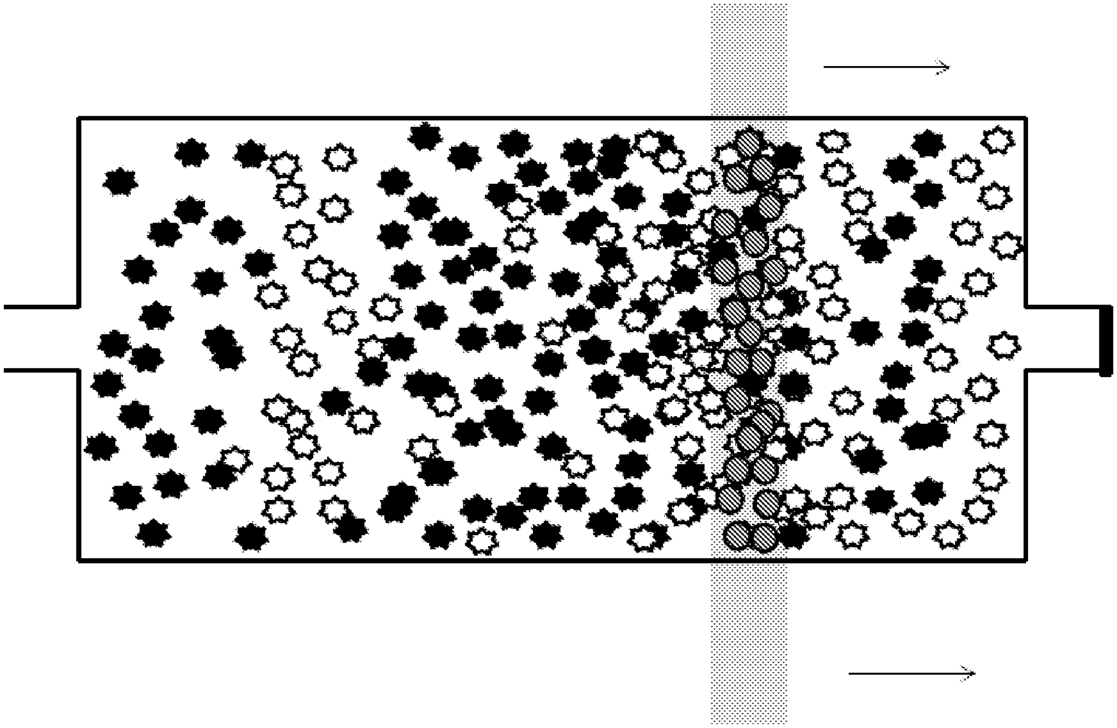
Figure 12F:
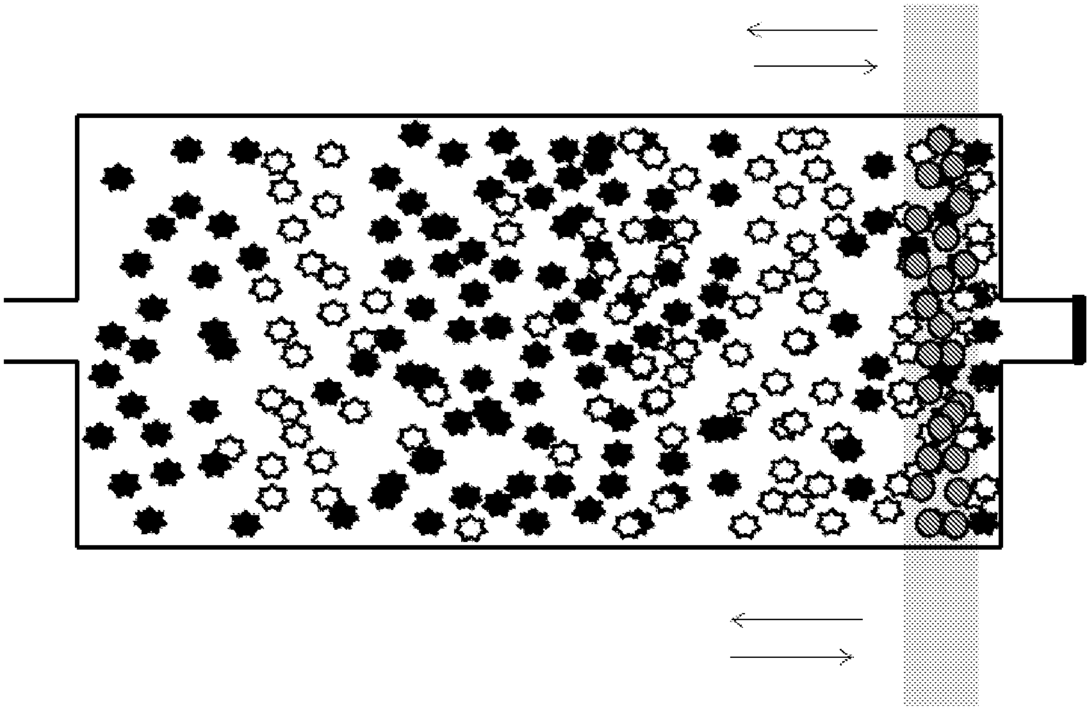
Figure 12G:
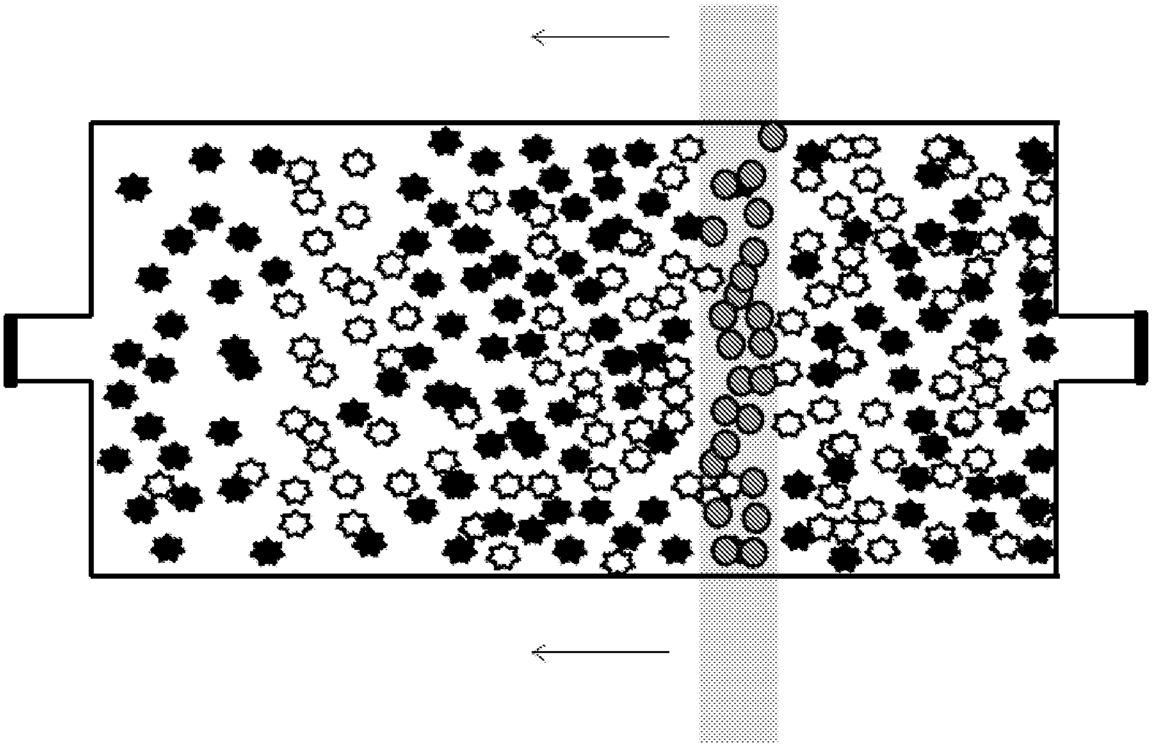
Figure 12H:
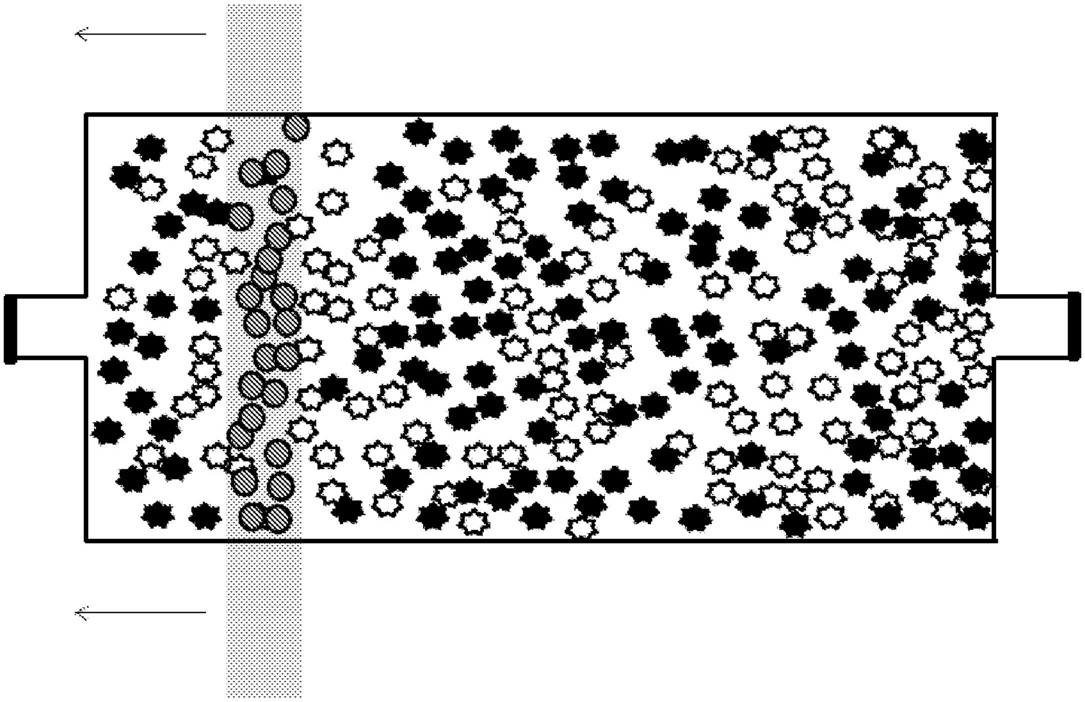
Figure 12I:
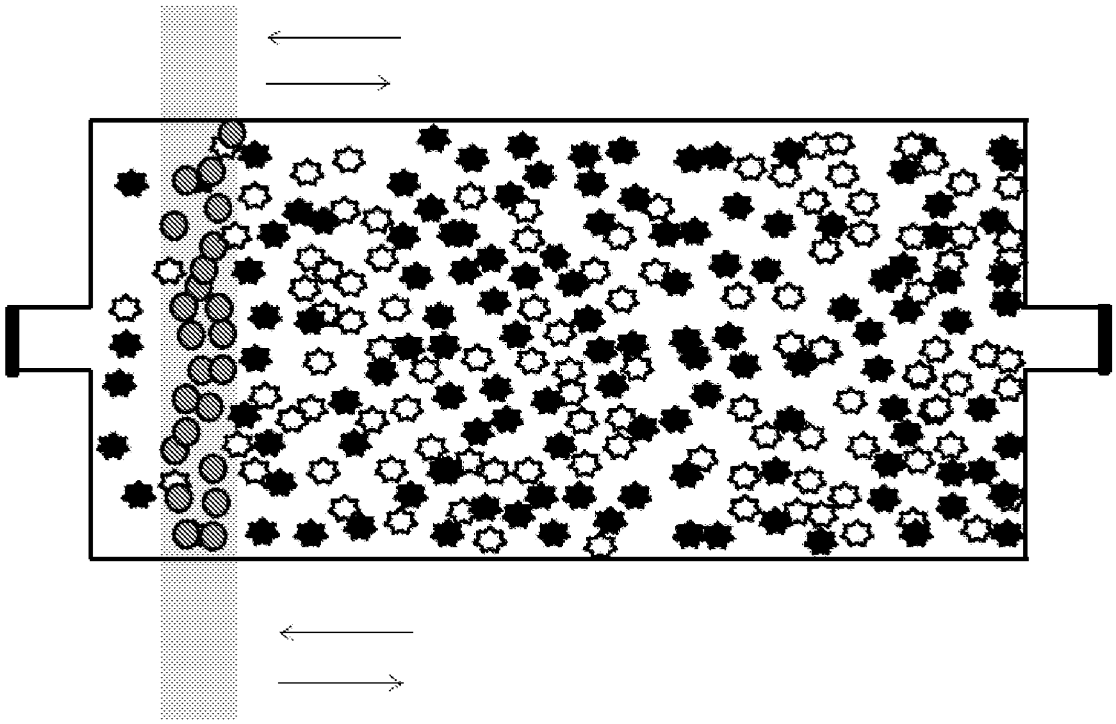

FIG. 8 shows a washing step in an experiment according to principles of the present invention. FIG. 9 is a graph showing the experimental results of sample purity after a number of washes or passes. FIGS. 10 and 11 further illustrate experimental data based on the number of washes or passes according to principles of the present invention.

It is contemplated that the chambers of the present invention, including the mixing chambers and the holding chambers, comprise a volume of about 10 nl to about 10 µl. In addition, this method is not limited to cell sorting, and may be applied to isolating target substrates, including, but not limited to molecules, cells, DNA, DNA fragments, RNA, and RNA fragments, small molecule, a nucleic acid (such as double stranded DNA, single stranded DNA, double stranded RNA, single stranded RNA or a fragment thereof), a peptide, a protein or an analog or derivative thereof.

FIG. 12 illustrates additional uses of chambers according to principles of the present invention. That is, a microfluidic chamber may be used to mix substrates within the chamber. The substrates may include, but are not limited to, molecules, cells, DNA, DNA fragments, RNA, and RNA fragments and the like. As illustrated in FIG. 12A, a plurality of a first target substrate and a plurality of a second target substrate are inserted into a microfluidic chamber. In the figure, the substrates are represented by the star-like particles. Magnetic beads are also provided in the chamber, as illustrated in FIG. 12B. As illustrated in FIG. 12C, a magnetic field is applied to the chamber. The magnetic beads stay in the proximity of the magnetic field. The magnetic field is then moved in a first direction, as illustrated in FIG. 12D. Movement of the magnetic field results in movement of the magnetic beads through the first and second target substrates, which causes the first and second substrates to intermix. The magnetic field can continue to be moved in the first direction and in a second direction until the first and second target substrates are mixed to a desired degree. Once the desired degree of mixing is achieved, the magnetic beads may be removed from the chamber. The chamber may have a volume of about 10 nl to about 10 µl. The magnetic field may be applied, for example, by bringing a permanent magnet, such as a Rare Earth magnet such as a Neodynium magnet, or an electro-magnet, into proximity of the first mixing chamber.

For example, in a method for isolating cells according to principles of the present invention includes providing a plurality of beads in a chamber, said beads capable of binding a cell-specific binding marker so as to attach to a specific cell-type; providing cells to the first chamber, the cells including cells of the specific cell-type, such that cells of the specific cell-type bind to specific beads of the plurality of beads; and retaining the cells of the specific cell-type bound to the specific beads in the chamber while removing cells not of the specific cell-type from the chamber. The cells may be retained in the chamber by filtration, electrophoresis, dielectrophoresis, electro-ostmotic flow, radiation pressure (e.g., photon pressure), surface immobilization, application of a magnetic field, or other known method.

In another example, the method may include providing a plurality of magnetic beads in a first chamber, said magnetic beads capable of binding a cell-specific binding marker so as to attach to a specific cell-type; providing cells to the first chamber, the cells including cells of the specific cell-type, such that cells of the specific cell-type bind to magnetic beads of the plurality of magnetic beads; applying a magnetic field to the first chamber and moving the magnetic field in a predetermined directions to transfer the magnetic beads to a second chamber, the second chamber in fluid communication with the first chamber; blocking fluid communication between the second chamber and the first chamber; washing the first chamber; unblocking fluid communication between the second chamber and the first chamber; removing the magnetic beads, including the magnetic beads bound to the cells of the specific cell-type, from the second chamber by applying the magnetic field to the second chamber in a second predetermined direction; and releasing the cells of the specific cell-type from the magnetic beads. In an aspect of the invention, the cells may be released from the magnetic beads by eluting. The chamber may comprise a volume of about 10 nl to about 10 µl. The magnetic field may be produced by known methods including activating a stationary magnet, bringing an electro-magnet or a permanent magnet into proximity of the chamber. The permanent magnet may comprise a rare earth magnet, such as a neodymium magnet. In the case where the magnetic beads are removed from the chamber, they may be removed from the second chamber by returning the magnetic beads to the first chamber. Then, the process may include blocking fluid communication between the second chamber and the first chamber; washing the second chamber; and unblocking fluid communication between the second chamber and the first chamber, prior to releasing the cells of the specific cell-type from the magnetic beads.

The method may also be used to isolate target substrates, such as the target substrates include at least one of a molecule, cell, DNA, DNA fragment, RNA, and RNA fragment, by, for example, (a) providing a plurality of magnetic beads to a plurality of respective first chambers, each respective plurality of magnetic beads provided to each first chamber containing only magnetic beads capable of binding to a respective target substrate such that each respective mixing chamber includes magnetic beads capable of binding to only one target substrate type; (b) providing a sample comprising multiple target substrate types to a plurality of respective first chambers; (c) applying a moveable magnetic field to transfer the magnetic beads, including any substrates bound thereto, between the first chambers and a second chambers; (d) blocking fluid communication between the second chambers and the first chambers; (e) washing select ones of the first chambers and the second chambers to remove non-bound substrates; (f) unblocking fluid communication between the second chambers and the first chambers; (g) repeating steps (c)-(f) a predetermined number of times; (h) releasing the respective target substrates from the magnetic beads. The system according the aspects of the present invention may also be used for mixing. For example, inserting a plurality of a first target substrate in a chamber; inserting a plurality of second target substrate in the chamber; inserting a plurality of magnetic beads in the chamber; applying a moveable magnetic field to the chamber; moving the magnetic field in a first direction; moving the magnetic field in a second direction different from the first direction; and removing the magnetic beads from the chamber.

As discussed above, a substrate-isolation platform according to the present invention may include a microfluidic chip, comprising a plurality of processing units, each processing unit comprising: an inlet port, a plurality of first chambers connected to the inlet port by a fluid channel, the fluid channel comprising a plurality of valves, a plurality of second chambers, each of the second chambers connected to a respective first chamber by a fluid channel, each fluid channel including a controllable blocking valve, and a plurality of respective outlet ports, each outlet port in fluid communication with a respective one of said second chambers and each outlet port including a blocking valve; and a magnet adjacent the microfluidic chip. The relative position of the magnet (or magnetic field) with respect to the microfluidic chip is variable. A valve control is capable of actuating certain ones of the controllable blocking valves in response to a control signal.

A method of integrated subtype purification and RNA-Seq may be performed on the platform. For example, by providing a plurality of first magnetic beads in a first chamber, said first magnetic beads capable of binding a cell-specific marker so as to attach a specific cell-type; providing cells to the first chamber, the cells including cells of the specific cell-type, such that cells of the specific cell-type bind to the first magnetic beads; applying a magnetic field to the first chamber and moving the magnetic field in a first predetermined direction to transfer the first magnetic beads to a second chamber, the second chamber in fluid communication with the first chamber; blocking fluid communication between the second chamber and the first chamber; washing the first chamber; unblocking fluid communication between the second chamber and the first chamber; releasing the cells from the first magnetic beads; removing the first magnetic beads from the second chamber by applying a magnetic field from the second chamber in a second predetermined direction; blocking fluid communication between the second chamber and the first chamber; lysing the cells; capturing target substrates from the lysed cells using second magnetic beads; applying a magnetic field to the second chamber and moving the magnetic field in a third predetermined direction to transfer the target substrates captured by the second magnetic beads to the first chamber; mixing the second magnetic beads and the captured target substrates with mRNA-seq reagents; cycling through a range of temperatures to create a PCR product; and applying solid phase reversible immobilization (SPRI) beads to the PCR product to clean up DNA.

Figure 13:
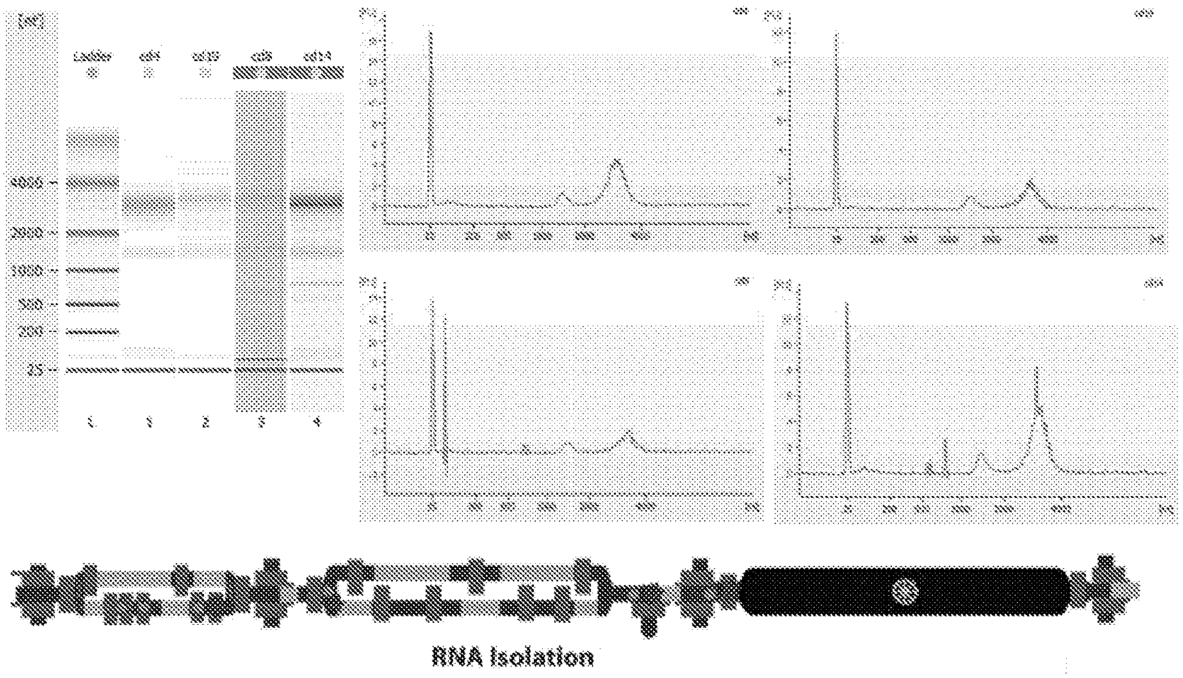
FIG. 13 illustrates operation of an embodiment of the present invention for RNA isolation.

FIG. 13 illustrates operation of an embodiment of the present invention for RNA isolation.

Figure 14:
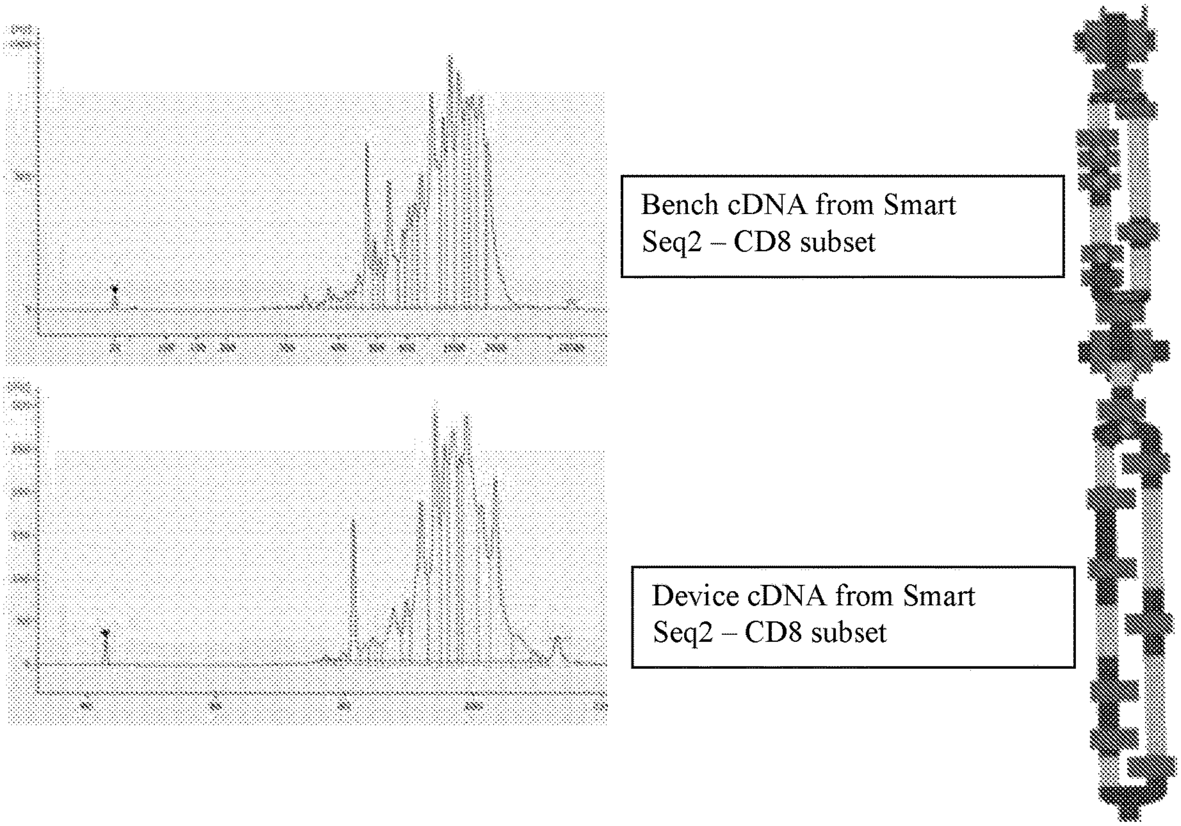
FIG. 14 illustrates results for Bench cDNA for Smart Seq2-CD8 subset Device cDNA for Smart Seq2-CD8 subset according to aspects of the present invention.

FIG. 14 illustrates results for Bench cDNA for Smart Seq2-CD8 subset Device cDNA for Smart Seq2-CD8 subset according to aspects of the present invention.

Figure 15:
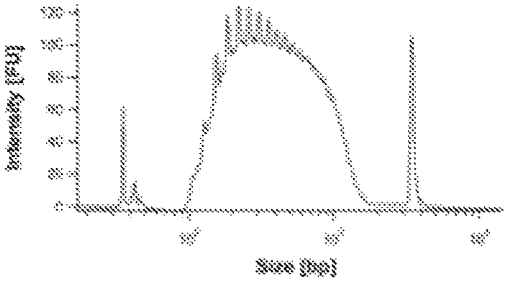
FIG. 15 illustrates results of Nextera XT Tagmentation for Benchtop control (Upper Graph) and Adapter Ligated Fragments Amplification for the Device (Lower Graph) according to aspects of the present invention.
Figure 15:
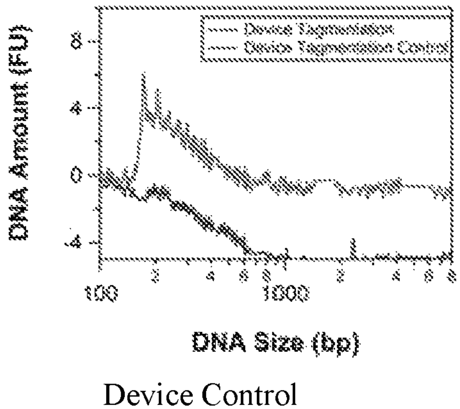

FIG. 15 illustrates results of Nextera XT Tagmentation for Benchtop control (Upper Graph) and Adapter Ligated Fragments Amplification for the Device (Lower Graph) according to aspects of the present invention.

Figure 16A:
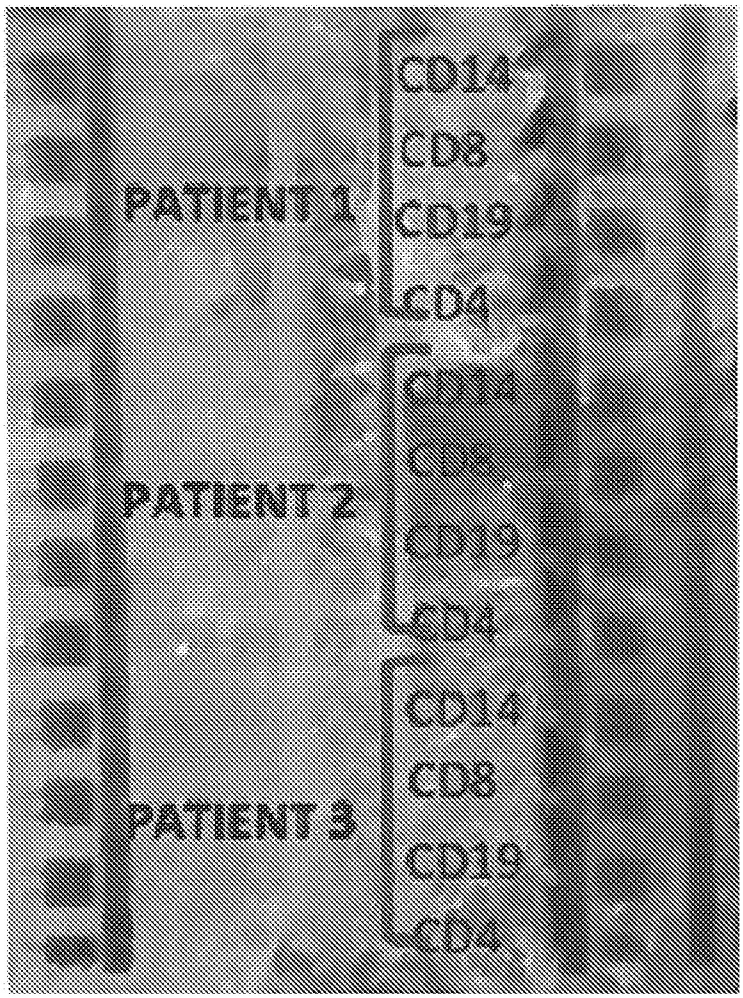
FIG. 16A illustrates 4 cell subtypes from 3 different patients resulting in 12 purified cell populations.
Figure 16B:
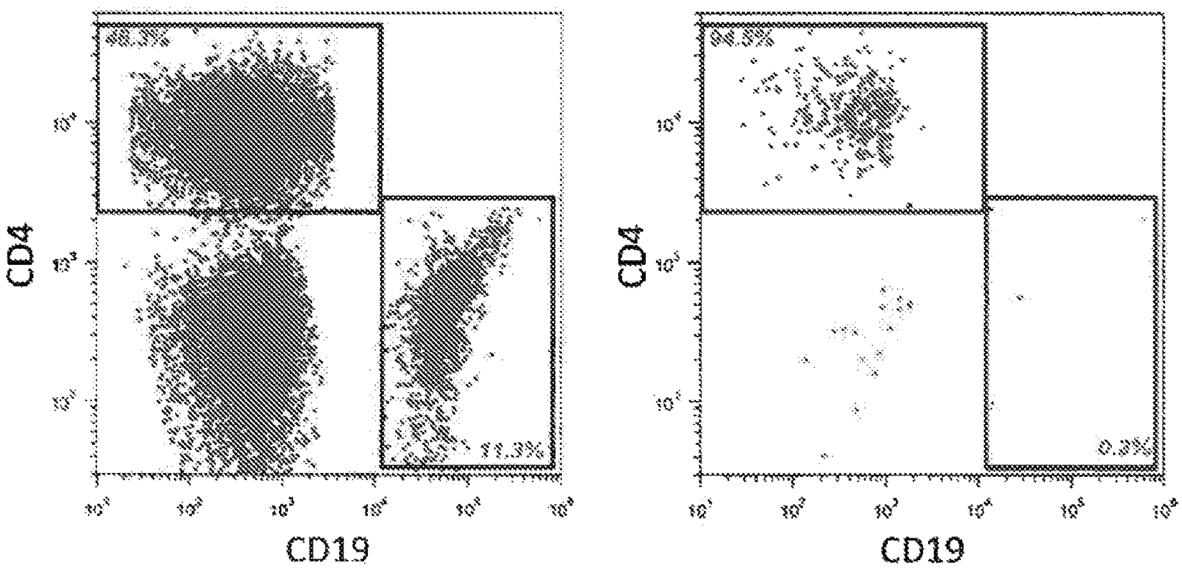
FIG. 16B illustrates results for optimizing MACS for the CD4 subset.
Figure 16C:
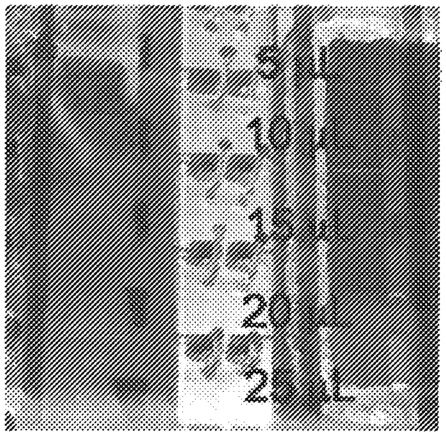
FIGS. 16C and 16D illustrate results from varying the quantity of beads and its effect on the purity and yield.
Figure 16D:
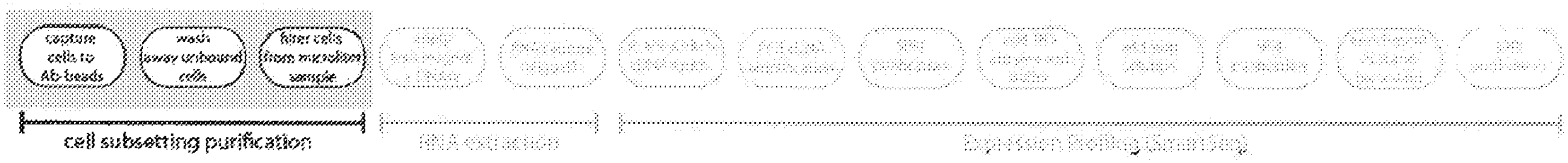

FIGS. 16A through 16D illustrate data from four types of cell surface markers from three different patients. FIGS. 9 and 10 (discussed previously) illustrate the step of optimizing the cell purification step by varying the wash steps. The results show the trade-off between yield and purity obtained from the number of washes. FIG. 16B demonstrates optimizing MACS of the CD4 subset. As the number of washes increased, the purity increased, however the yield decreased. FIG. 16C illustrates varying the quantity of beads and its effect on the purity and yield. Counterintuitively, higher yields are obtained in some cases with a smaller amount of beads.

Figure 17:
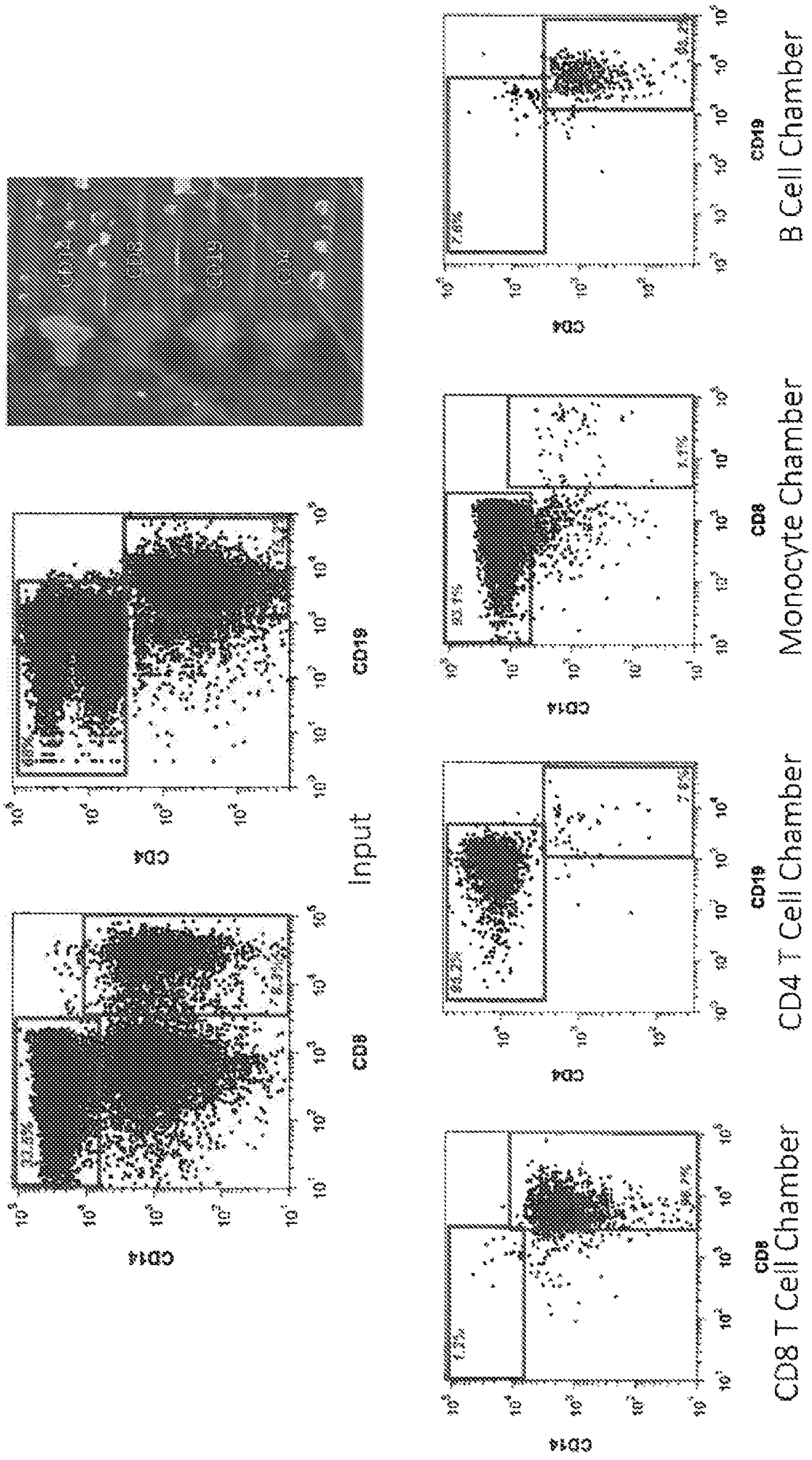
FIG. 17 illustrates monocytes, CD8+ T cell, CD4+ T cell, and B cell isolation from PBMCs at over 90% purity using a 100,000 PBMC input device.

FIG. 17 illustrates the aforementioned four subtypes of cellular markers. The panels show isolation of T cells, B cells, and monocytes at over 90% purity. The four different channels on the flow cytometers are correlated to four different markers. Each panel shows the output (the percentage of cells) that fall into each gate. The purity observed demonstrates that it is possible to conduct single positive selection and single negative selection. In order to access the particular subsets of interest, positive and negative selection are needed.

Figure 18A:
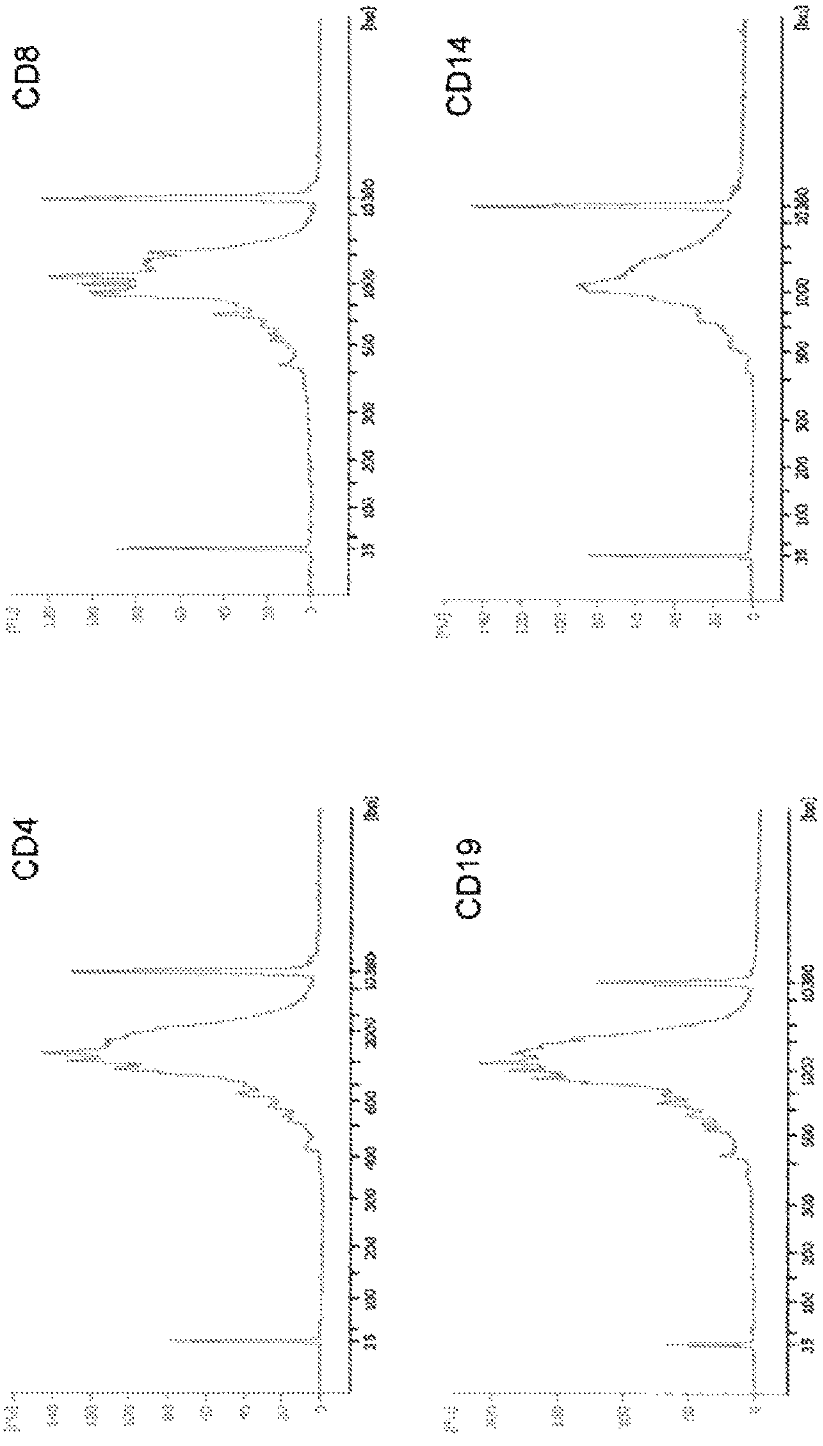
FIGS. 18A and 18B illustrate cDNA produced on-chip from on-chip purified cell subsets further validating the success of this workflow.
Figure 18B:
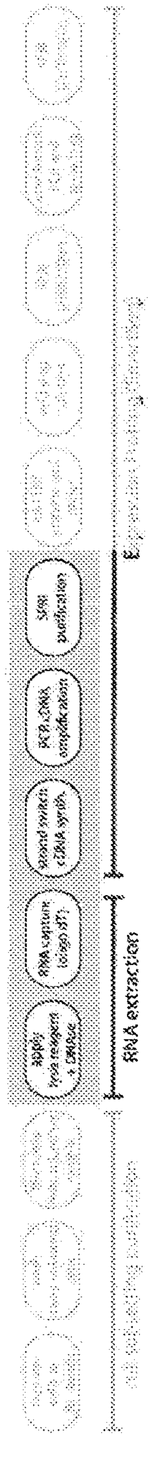

FIGS. 18A and 18B further validating the size distribution of the cDNA obtained and confirming the success of this workflow.

Figure 19A:
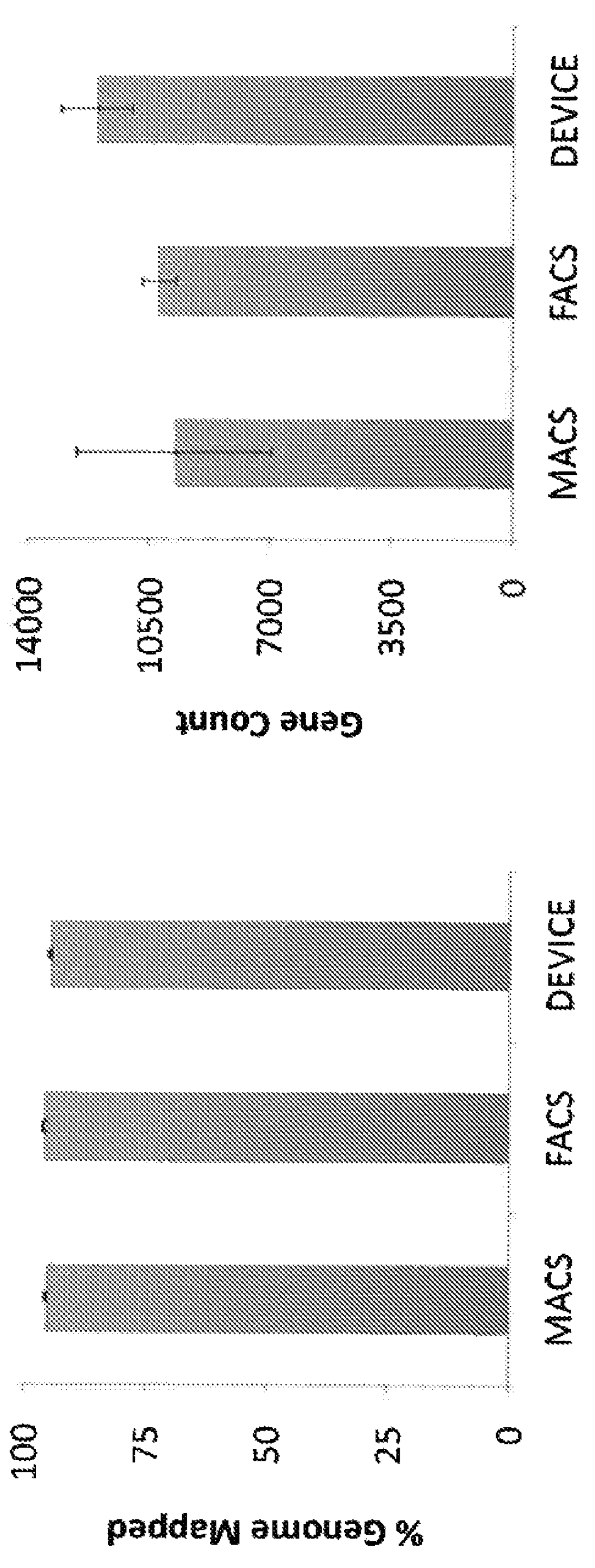
FIGS. 19A and 19B illustrate results which demonstrate the fully-integrated workflow provides high-quality subset-specific RNA-seq data.
Figure 19B:
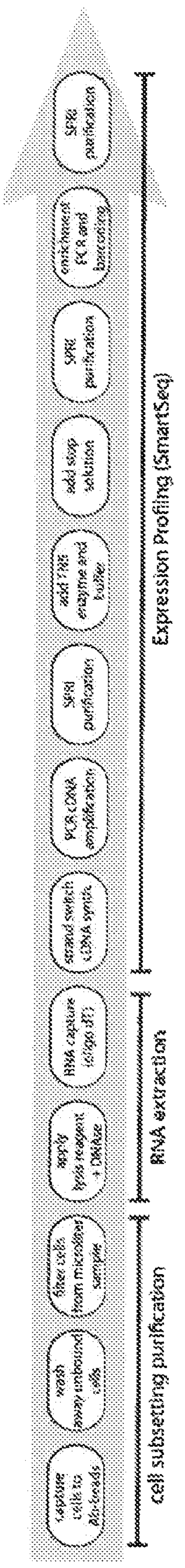
Figures 20A, 20B, 20C, 20D:
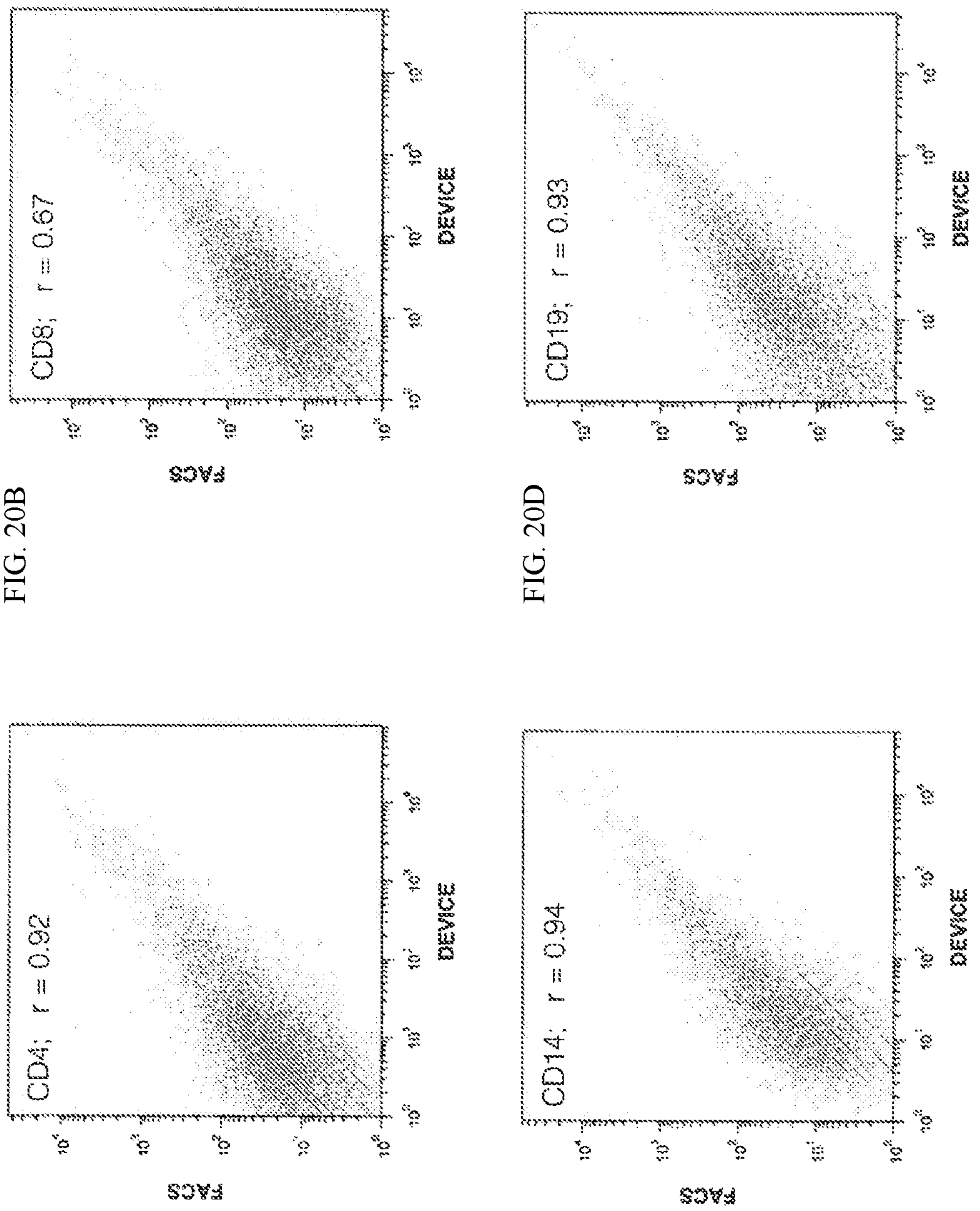
FIGS. 20A to 20D illustrate that device-purified and positive-control FACS purified subsets correlate strongly.
Figure 21A:
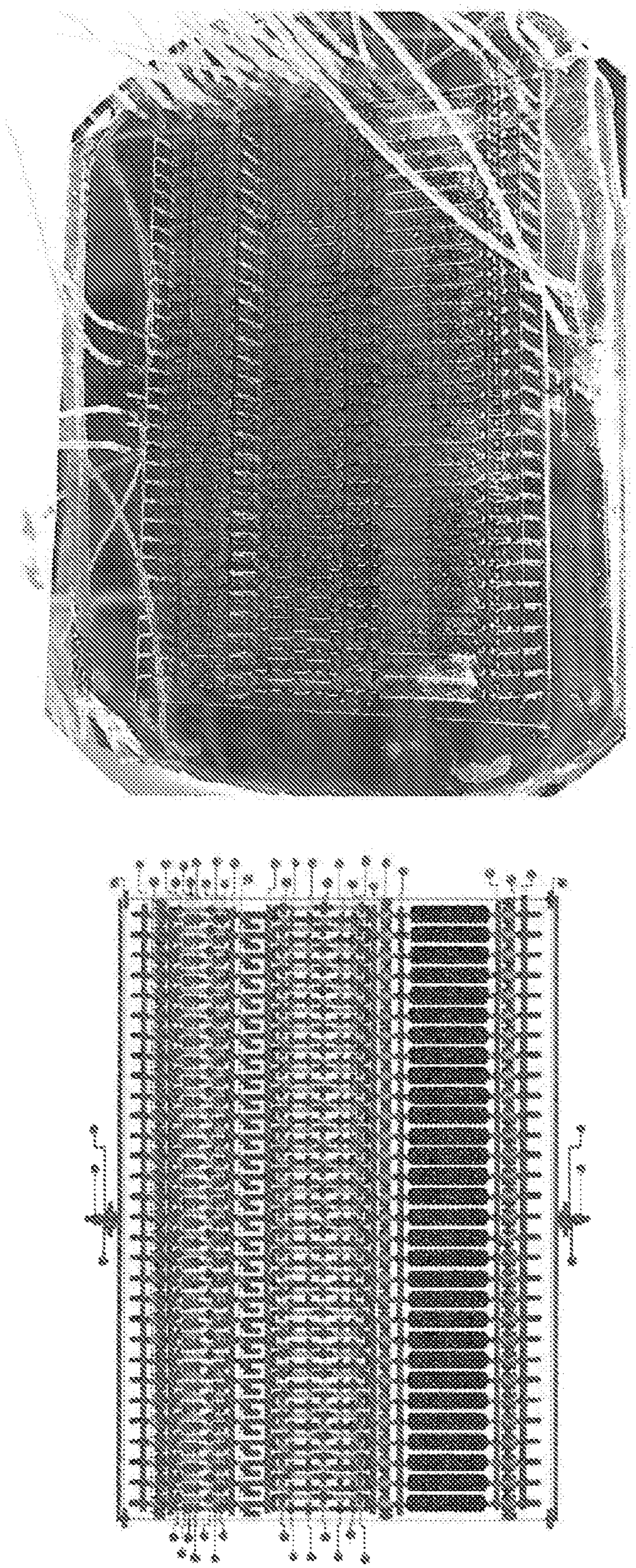
FIGS. 21A and 21B illustrate a next-generation device with 30-plex subset capacity.
Figure 21B:
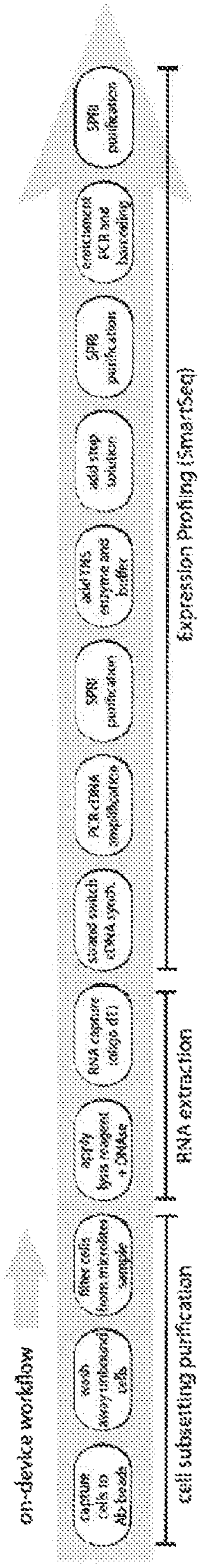

FIG. 19A compares the device described and enabled by the present application to conventional methods as a control. The microfluidic device illustrates that the coverage of the transcriptome is comparable to other methods such as MACS and FACS. The same holds true for the number of genes detected, again confirming and validating the results obtained herein.

FIGS. 20A through 20D quantitatively compares the positive control (FACS) with the results obtained by the device described herein. For each of the CD4, CD14, and CD19 cell subsets, the results obtained with the device were strongly correlated with the FACS purified subsets.

Applicants found that restricting the amount of beads in some steps (e.g. cell capture or RNA capture) provides a method to standardize and normalize the data. The present application also provides a method of performing thermocycling on the chip. Applicants discovered that through varying the substrate of the chip, such as by using material including but not limited to quartz, silica, or other materials known in the art to provide good thermal conductivity, it was possible to provide thermocycling on the chip. Thermal conductivity, k, λ, or κ, is the property of a material to conduct heat which is evaluated in terms of Fourier's Law for heat conduction. In one aspect of the invention, two characteristics for facilitating thermocycling on chips are: (1) thin material and (2) material that possesses good thermal conductivity. When the chip substrate possesses both qualities it was found that thermocycling was both efficient and robust. It will also be appreciated that the number of PCR cycles used in the thermocycling will impact its efficiency.

Library Preparation and Droplet Microfluidics for Rapid, Large-Scale Processing

Principles of the present invention allow for library construction. For example, Additional advantages of the disclosed invention provides an ability to create a library of emulsion droplets on demand with the further capability of manipulating the droplets. To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination. A cell library element may include, but is not limited to, hybridomas. B-cells, primary cells, cultured cell lines, cancer cells, stem cells, cells obtained from tissue, or any other cell type.

To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the microfluidic channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Fluidic droplets may be screened or sorted within a fluidic system by altering the flow of the liquid containing the droplets. For instance, a fluidic droplet may be steered or sorted by directing the liquid surrounding the fluidic droplet into a first channel, a second channel, etc. Pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another embodiment, the expansion and/or contraction of the liquid reservoir may be combined with other flow-controlling devices and methods, e.g., as described herein. Non-limiting examples of devices able to cause the expansion and/or contraction of a liquid reservoir include pistons.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, microbeads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element may include, but is not limited to, hybridomas, B-cells, primary cells, cultured cell lines, cancer cells, stem cells, cells obtained from tissue, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or following, encapsulation produces a clonal library element.

A bead based library element may contain one or more microbeads, of a given type and may also contain other reagents, such as antibodies, enzymes or other proteins. In the case where all library elements contain different types of microbeads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids.

Often it is desirable to have exactly one cell per droplet with only a few droplets containing more than one cell when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell.

Examples of droplet libraries are collections of droplets that have different contents, ranging from microbeads, cells, small molecules, DNA, primers, antibodies. Smaller droplets may be in the order of femtoliter (fL) volume drops, which are especially contemplated with the droplet dispensors. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the emulsion libraries may be contained within an immiscible oil which may comprise at least one fluorosurfactant. The fluorosurfactant may be within immiscible fluorocarbon oil is a block copolymer consisting of one or more perfluorinated polyether (PFPE) blocks and one or more polyethylene glycol (PEG) blocks. The fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that may be utilized in the droplet libraries are described in greater detail herein.

An emulsion library may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. Forming the emulsion library may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or microbeads), may be pooled in a single source contained in the same medium. After the initial pooling, the cells or microbeads are then encapsulated in droplets to generate a library of droplets wherein each droplet with a different type of bead or cell is a different library element. The dilution of the initial solution enables the encapsulation process. The droplets formed will either contain a single cell or bead or will not contain anything, i.e., be empty. The droplets formed will contain multiple copies of a library element. The cells or microbeads being encapsulated are generally variants on the same type of cell or bead. In one example, the cells may comprise cancer cells of a tissue biopsy, and each cell type is encapsulated to be screened for genomic data or against different drug therapies. Another example is that $10^{11}$ or $10^{15}$ different type of bacteria; each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 μm droplets were made at 10 kHz per second. Formation of these libraries rely on limiting dilutions.

Methods involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc. The content of each of which is incorporated by reference herein in its entirety.

The carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

The droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

Applications of microfluidic devices may include use for the dynamic generation of molecular barcodes (e.g., DNA oligonucleotides, flurophores, etc.) either independent from or in concert with the controlled delivery of various compounds of interest (drugs, small molecules, RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques facilitate efforts to perform studies that require data resolution at the single cell (or single molecule) level and in a cost effective manner. A high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion has previously been disclosed in International Patent Application No. PCT/US2014/028941, which is hereby incorporated by reference in its entirety for all purposes as if fully set forth herein, to allow dynamic tracking of individual cells and droplet treatments/combinations during life cycle experiments and an ability to create a library of emulsion droplets on demand with the further capability of manipulating the droplets through the disclosed process(es). Thus, provide dynamic tracking of the droplets and create a history of droplet deployment and application in a single cell based environment may be possible.

Droplet generation and deployment is produced via a dynamic indexing strategy and in a controlled fashion. Microfluidic devices may provide the capability of microdroplets that be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays.

There is a method for preparing uniquely barcoded mRNA capture microbeads, which has a unique barcode and diameter suitable for microfluidic devices comprising: 1) performing reverse phosphoramidite synthesis on the surface of the bead in a pool-and-split fashion, such that in each cycle of synthesis the microbeads are split into four reactions with one of the four canonical nucleotides (T, C, G, or A) or unique oligonucleotides of length two or more bases; 2) repeating this process a large number of times, at least two, and optimally more than twelve, such that, in the latter, there are more than 16 million unique barcodes on the surface of each bead in the pool. (See http://www.ncbi.nlm.nih.gov/pmc/articles/PMC206447)

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code.

The label may be light sensitive, wherein the label is light-activated and/or light cleaves the one or more linkers to release the molecular cargo. The light-activated molecular cargo may be a major light-harvesting complex (LHCII). The fluorescent label may induce free radical formation.

There are methods to enable high throughput and high resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. Single cells or single organelles or single molecules (proteins, RNA, DNA) are encapsulated into uniform droplets from an aqueous solution/dispersion. Multiple cells or multiple molecules may take the place of single cells or single molecules. The aqueous droplets of volume ranging from 1 pL to 10 nL work as individual reactors. Single cells in droplets which can be processed and analyzed in a single run.

In one embodiment, the labeling ligand may comprise an antibody or an antibody fragment, such as but not limited to, a nanobody, Fab, Fab', (Fab')2, Fv, ScFv, diabody, triabody, tetrabody, Bis-scFv, minibody, Fab2, or Fab3 fragment.

In another embodiment, the labeling ligand may comprise an aptamer.

The labeling ligand may comprise a nucleotide sequence complementary to a target sequence.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

A detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. The detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

One or more other species may be associated with the tags. In particular, nucleic acids released by a lysed cell may be ligated to one or more tags. These may include, for example, chromosomal DNA, RNA transcripts, tRNA, mRNA, mitochondrial DNA, or the like. Such nucleic acids may be sequenced, in addition to sequencing the tags themselves, which may yield information about the nucleic acid profile of the cells, which can be associated with the tags, or the conditions that the corresponding droplet or cell was exposed to.

A high-throughput single-cell RNA-Seq and/or targeted nucleic acid profiling (for example, sequencing, quantitative reverse transcription polymerase chain reaction, and the like) where the RNAs from different cells are tagged individually, allows a single library to be created while retaining the cell identity of each read. In this regard, technology of U.S. provisional patent application Ser. No. 62/048,227 filed Sep. 9, 2014, the disclosure of which is incorporated by reference, may be used in or as to the invention. A combination of molecular barcoding and emulsion-based microfluidics to isolate, lyse, barcode, and prepare nucleic acids from individual cells in high-throughput is used. Microfluidic devices (for example, fabricated in polydimethylsiloxane), sub-nanoliter reverse emulsion droplets. These droplets are used to co-encapsulate nucleic acids with a barcoded capture bead. Each bead, for example, is uniquely barcoded so that each drop and its contents are distinguishable. The nucleic acids may come from any source known in the art, such as for example, those which come from a single cell, a pair of cells, a cellular lysate, or a solution. The cells may be isolated and lysed according to the aspects of the present invention and encapsulated in the droplet. To load single cells and barcoded beads into these droplets with Poisson statistics, 100,000 to 10 million such beads are needed to barcode ~10,000-100,000 cells. In this regard there can be a single-cell sequencing library which may comprise: merging one uniquely barcoded mRNA capture microbead with a single-cell in an emulsion droplet having a diameter of 75-125 μm; lysing the cell to make its RNA accessible for capturing by hybridization onto RNA capture microbead; performing a reverse transcription either inside or outside the emulsion droplet to convert the cell's mRNA to a first strand cDNA that is covalently linked to the mRNA capture microbead; pooling the cDNA-attached microbeads from all cells; and preparing and sequencing a single composite RNA-Seq library. In this regard reference is made to Macosko et al., 2015, "Highly Parallel Genome-wide Expression Profiling of Individual Cells Using Nanoliter Droplets" Cell 161, 1202-1214 and Klein et al., 2015, "Droplet Barcoding for Single-Cell Transcriptomics Applied to Embryonic Stem Cells" Cell 161, 1187-1201 all the contents and disclosure of each of which are herein incorporated by reference in their entirety.

The RNA sequencing may involve single nucleus RNA sequencing. In this regard reference is made to Swiech et al., 2014, "In vivo interrogation of gene function in the mammalian brain using CRISPR-Cas9" Nature Biotechnology 33, 102-106.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added. Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. A fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code. Advantageously, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation. Advantageously, agents may be uniquely labeled in a dynamic manner (see, e.g., U.S. provisional patent application Ser. No. 61/703,884 filed Sep. 21, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached. Oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the non-nucleic acid detectable moiety. A detectable oligonucleotide tag may comprise one or more non-oligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art. Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties. A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag. One or more other species may be associated with the tags. In particular, nucleic acids released by a lysed cell may be ligated to one or more tags. These may include, for example, chromosomal DNA, RNA transcripts, tRNA, mRNA, mitochondrial DNA, or the like. Such nucleic acids may be sequenced, in addition to sequencing the tags themselves, which may yield information about the nucleic acid profile of the cells, which can be associated with the tags, or the conditions that the corresponding droplet or cell was exposed to.

The invention can thus involve isolating target substrates forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc. The content of each of which is incorporated by reference herein in its entirety. The present invention may relates to systems and methods for manipulating droplets within a high throughput microfluidic system. A microfluid droplet encapsulates a differentiated cell. The cell is lysed and its mRNA is hybridized onto a capture bead containing barcoded oligo dT primers on the surface, all inside the droplet. The barcode is covalently attached to the capture bead via a flexible multi-atom linker like PEG. In a preferred embodiment, the droplets are broken by addition of a fluorosurfactant (like perfluorooctanol), washed, and collected. A reverse transcription (RT) reaction is then performed to convert each cell's mRNA into a first strand cDNA that is both uniquely barcoded and covalently linked to the mRNA capture bead. Subsequently, a universal primer via a template switching reaction is amended using conventional library preparation protocols to prepare an RNA-Seq library. Since all of the mRNA from any given cell is uniquely barcoded, a single library is sequenced and then computationally resolved to determine which mRNAs came from which cells. In this way, through a single sequencing run, tens of thousands (or more) of distinguishable transcriptomes can be simultaneously obtained. The oligonucleotide sequence may be generated on the bead surface. During these cycles, beads were removed from the synthesis column, pooled, and aliquoted into four equal portions by mass; these bead aliquots were then placed in a separate synthesis column and reacted with either dG, dC, dT, or dA phosphoramidite. In other instances, dinucleotide, trinucleotides, or oligonucleotides that are greater in length are used, in other instances, the oligo-dT tail is replaced by gene specific oligonucleotides to prime specific targets (singular or plural), random sequences of any length for the capture of all or specific RNAs. This process was repeated 12 times for a total of $4^{12}$=16,777,216 unique barcode sequences. Upon completion of these cycles, 8 cycles of degenerate oligonucleotide synthesis were performed on all the beads, followed by 30 cycles of dT addition. In other embodiments, the degenerate synthesis is omitted, shortened (less than 8 cycles), or extended (more than 8 cycles); in others, the 30 cycles of dT addition are replaced with gene specific primers (single target or many targets) or a degenerate sequence. The aforementioned microfluidic system is regarded as the reagent delivery system microfluidic library printer or droplet library printing system of the present invention. Droplets are formed as sample fluid flows from droplet generator which contains lysis reagent and barcodes through microfluidic outlet channel which contains oil, towards junction. Defined volumes of loaded reagent emulsion, corresponding to defined numbers of droplets, are dispensed on-demand into the flow stream of carrier fluid. The sample fluid may typically comprise an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid may include one that is immiscible with the sample fluid. The carrier fluid can be a non-polar solvent, decane (e.g., tetradecane or hexadecane), fluorocarbon oil, silicone oil, an inert oil such as hydrocarbon, or another oil (for example, mineral oil). The carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing. Droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In some cases, an apparatus for creating a single-cell sequencing library via a microfluidic system provides for volume-driven flow, wherein constant volumes are injected over time. The pressure in fluidic channels is a function of injection rate and channel dimensions. In one embodiment, the device provides an oil/surfactant inlet; an inlet for an analyte; a filter, an inlet for mRNA capture microbeads and lysis reagent; a carrier fluid channel which connects the inlets; a resistor; a constriction for droplet pinch-off; a mixer; and an outlet for drops. In an embodiment the invention provides apparatus for creating a single-cell sequencing library via a microfluidic system, which may comprise: an oil-surfactant inlet which may comprise a filter and a carrier fluid channel, wherein said carrier fluid channel may further comprise a resistor; an inlet for an analyte which may comprise a filter and a carrier fluid channel, wherein said carrier fluid channel may further comprise a resistor; an inlet for mRNA capture microbeads and lysis reagent which may comprise a filter and a carrier fluid channel, wherein said carrier fluid channel further may comprise a resistor; said carrier fluid channels have a carrier fluid flowing therein at an adjustable or predetermined flow rate; wherein each said carrier fluid channels merge at a junction; and said junction being connected to a mixer, which contains an outlet for drops. Accordingly, an apparatus for creating a single-cell sequencing library via a microfluidic system or microfluidic flow scheme for single-cell RNA-seq is envisioned. Two channels, one carrying cell suspensions, and the other carrying uniquely barcoded mRNA capture bead, lysis buffer and library preparation reagents meet at a junction and is immediately co-encapsulated in an inert carrier oil, at the rate of one cell and one bead per drop. In each drop, using the bead's barcode tagged oligonucleotides as cDNA template, each mRNA is tagged with a unique, cell-specific identifier. The invention also encompasses use of a Drop-Seq library of a mixture of mouse and human cells. The carrier fluid may be caused to flow through the outlet channel so that the surfactant in the carrier fluid coats the channel walls. The fluorosurfactant can be prepared by reacting the perfluorinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Fluorinert (3M)), which then serves as the carrier fluid. Activation of sample fluid reservoirs to produce regent droplets is based on the concept of dynamic reagent delivery (e.g., combinatorial barcoding) via an on demand capability. The on demand feature may be provided by one of a variety of technical capabilities for releasing delivery droplets to a primary droplet, as described herein. From this disclosure and herein cited documents and knowledge in the art, it is within the ambit of the skilled person to develop flow rates, channel lengths, and channel geometries, and establish droplets containing random or specified reagent combinations can be generated on demand and merged with the "reaction chamber" droplets containing the samples/cells/substrates of interest. By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioinformatically record information can be found at US Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012. Accordingly, in or as to the invention it is envisioned that there can be the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. The invention envisions a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Being able to dynamically track individual cells and droplet treatments/combinations during life cycle experiments, and having an ability to create a library of emulsion droplets on demand with the further capability of manipulating the droplets through the disclosed process(es) are advantageous. In the practice of the invention there can be dynamic tracking of the droplets and create a history of droplet deployment and application in a single cell based environment. Droplet generation and deployment is produced via a dynamic indexing strategy and in a controlled fashion in accordance with disclosed embodiments of the present invention. Microdroplets can be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays. A plurality of biological assays as well as biological synthesis are contemplated. Polymerase chain reactions (PCR) are contemplated (see, e.g., US Patent Publication No. 20120219947). Methods of the invention may be used for merging sample fluids for conducting any type of chemical reaction or any type of biological assay. There may be merging sample fluids for conducting an amplification reaction in a droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyper-branched rolling circle amplification. In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence. To effect amplification, primers are annealed to their complementary sequence within the target molecule. Following annealing, the primers are extended with a polymerase so as to form a new pair of complementary strands. The steps of denaturation, primer annealing and polymerase extension may be repeated many times (i.e., denaturation, annealing and extension constitute one cycle; there may be numerous cycles) to obtain a high concentration of an amplified segment of a desired target sequence. The length of the amplified segment of the desired target sequence is determined by relative positions of the primers with respect to each other, and therefore, this length is a controllable parameter. Methods for performing PCR in droplets are shown for example in Link et al. (U.S. Patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety. The first sample fluid contains nucleic acid templates. Droplets of the first sample fluid are formed as described above. Those droplets will include the nucleic acid templates. In certain embodiments, the droplets will include only a single nucleic acid template, and thus digital PCR may be conducted. The second sample fluid contains reagents for the PCR reaction. Such reagents generally include Taq polymerase, deoxynucleotides of type A, C, G and T, magnesium chloride, and forward and reverse primers, all suspended within an aqueous buffer. The second fluid also includes detectably labeled probes for detection of the amplified target nucleic acid, the details of which are discussed below. This type of partitioning of the reagents between the two sample fluids is not the only possibility. In some instances, the first sample fluid will include some or all of the reagents necessary for the PCR whereas the second sample fluid will contain the balance of the reagents necessary for the PCR together with the detection probes. Primers may be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers may also be obtained from commercial sources such as Operon Technologies, Amersham Pharmacia Biotech, Sigma, and Life Technologies. The primers may have an identical melting temperature. The lengths of the primers may be extended or shortened at the 5' end or the 3' end to produce primers with desired melting temperatures. Also, the annealing position of each primer pair may be designed such that the sequence and, length of the primer pairs yield the desired melting temperature. The simplest equation for determining the melting temperature of primers smaller than 25 base pairs is the Wallace Rule (Td=2(A+T)+4(G+C)). Computer programs may also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

A droplet containing the nucleic acid can be merged with the PCR reagents in the second fluid, producing a droplet that includes Taq polymerase, deoxynucleotides of type A, C, G and T, magnesium chloride, forward and reverse primers, detectably labeled probes, and the target nucleic acid. Once mixed droplets have been produced, the droplets are thermal cycled, resulting in amplification of the target nucleic acid in each droplet. Droplets may be flowed through a channel in a serpentine path between heating and cooling lines to amplify the nucleic acid in the droplet. The width and depth of the channel may be adjusted to set the residence time at each temperature, which may be controlled to anywhere between less than a second and minutes. The three temperature zones may be used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, N.Y., 2001). The three temperature zones can be controlled to have temperatures as follows: 95° C. (TH), 55° C. (TL), 72° C. (TM). The prepared sample droplets flow through the channel at a controlled rate. The sample droplets first pass the initial denaturation zone (TH) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme. The nucleic acids undergo the same thermal cycling and chemical reaction as the droplets pass through each thermal cycle as they flow through the channel. The total number of cycles in the device is easily altered by an extension of thermal zones. The sample undergoes the same thermal cycling and chemical reaction as it passes through N amplification cycles of the complete thermal device. In other aspects, the temperature zones are controlled to achieve two individual temperature zones for a PCR reaction. In certain embodiments, the two temperature zones are controlled to have temperatures as follows: 95° C. (TH) and 60° C. (TL). The sample droplet optionally flows through an initial preheat zone before entering thermal cycling. The preheat zone may be important for some chemistry for activation and also to ensure that double stranded nucleic acid in the droplets is fully denatured before the thermal cycling reaction begins. In an exemplary embodiment, the preheat dwell length results in approximately 10 minutes preheat of the droplets at the higher temperature. The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing. After amplification, droplets may be flowed to a detection module for detection of amplification products. The droplets may be individually analyzed and detected using any methods known in the art, such as detecting for the presence or amount of a reporter. Generally, a detection module is in communication with one or more detection apparatuses. Detection apparatuses may be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES AND METHODOLOGY

Microfluidic Device Fabrication. Soft Lithography.

Microfluidic devices were fabricated by multilayer soft lithography of PDMS, a transparent silicone elastomer, on a mold comprised of a silicon wafer patterned with photoresist. Separate molds were used to cast a control layer of height 50 μm and a flow layer of height 70 μm. The two layers were partially cured, aligned manually and thermally bonded by further curing. Inlet ports were punched and the two-layer PDMS device was bonded to a glass slide after activation by air plasma exposure.

Device production utilized standard soft lithography protocols. PDMS (Momentive) was mixed at 10:1 silicone to cross-linker ratio in a Thinky AR250 mixer, poured onto the flow layer mold, degassed in a vacuum chamber and cured by baking for 20 min at 80° C. PDMS at a 10:1 silicone to cross-linker ratio was spin coated on the valve layer mold to a height of 20 μm, then baked at 80° C. for 6 min. The two layers were aligned under a stereomicroscope (Nikon), and further baked for 6 h at 105° C. to complete thermal bonding. Inlet holes were punched into the two-layered PDMS device (Syneo, ID 660 mm tips) on the designated input/output port features. The device was then exposed to atmospheric plasma for 2 min at a pressure of 1.3 mbar (Diener ATTO), bonded to a clean glass slide and baked for 3 h at 80° C.

Microfluidic Device Fabrication. Hard Lithography.

Device production utilized standard hard lithography protocols to afford a device with three different layers (rectangular, tank, and round). The flow layer mold was patterned accordingly: (1) rectangular layer 70 μm, (2) tank layer 200 μm, (3) curved layer 70 μm, features. The rectangular features were made by spin coating SU-8 2075 (70 μm and 100 μm) and 2015 (15 μm and 30 μm) photoresists (Microchem) on a silicon wafer. The coated wafers were patterned by ultraviolet exposure (OAI 206 mask aligner) through a mask printed at 20,000 dpi (Fineline; see Autocad design files for each layer in supplementary material), followed by feature development in SU-8 developer (Microchem). The rounded features were produced by spin coating AZ-40XT photoresist (AZ Electronic Materials) after coating with hexamethyldisilazane (Sigma) and air-drying, patterning the wafer with UV exposure and a mask, developing in the AZ MIF 300 developer (AZ Electronic Materials), and heating for 10 min at 105° C. to form rounded features. Binding Buffer solution utilized: 20 mM Tris-HCl, 1.0 M LiCl, 2 mM EDTA, pH 7.5.

Microfluidic Subsetting and RNA Seq Library Construction.

10 µl of antibody coated dynabeads were washed with 200 µl of cell isolation buffer (2.5 mM EDTA ultra pure, 10% UltrapureBSA). Following this, the beads were re-suspended in 10 µl of the cell isolation buffer. Prior to loading the beads into the device, the device was completely filled with pluronic acid (Sigma-Aldrich) and left to stand for 10 min. The solution was then replaced with cell isolation buffer. Antibody coated beads at a volume of 5 µl were pulled into the device tank with the aid of a magnet. This was followed by the loading of the cells into the tank. The cells and beads were mixed by passing a magnet up and down the tank for 10 min. Non-target cells were washed out by holding the magnet under the chamber while individually opening each reaction chamber (repeat 5 times to achieve high purity). Once a high purity of the desired cell type was attained, the cells were allowed to migrate into the ring where they were lysed for 10 mins at 37° C. while continuously mixed with the valves. Following lysis, the cell isolation beads were replaced with oligo (dT) beads. These beads were used to pull down the mRNA by mixing at room temperature for 5 mins. The beads were washed with wash buffer (10 mM Tris-HCl, pH 7.5, 0.15 M LiCl, 1 mM EDTA 10 mM Tris-HCl, pH 7.5) twice and resuspended into the Smart Seq2 reagents. The device was then placed on a thermocycler where the following program was run: 52° C. for 5 min, 45° C. for 90 minutes, followed by 10 cycles of (52° C. for 2.20 min, 45° C. for 2.2 min), then heat inactivation at 72° C. for 15 min. At this point the DNA is still on the beads, hence the beads were moved to half of the ring and the unused side of the ring replaced with PCR master mix. The beads and PCR reagents were allowed to mix for 5 min, then the device was placed on the thermocycler. The thermocycler was programmed as follows: 99.5° C. for 3 min 18-22 cycles of (99.5° C. for 15 sec, 67° C. for 20 sec, 75° C. for 6 min), final extension at 72° C. for 5 min. At this point the DNA is no longer attached to the beads, consequently these beads were discarded and SPRI beads allowed into the device for the clean-up step. Once the SPRI beads had pulled down the DNA, the beads were washed with ethanol and re-suspended in TE-buffer. The DNA was then released from the device for quantification and tagmentation steps. This process relies solely on 3 external systems, the controller, a magnetic bar and a thermocycler. With the aid of a robotic arm, this process can be automated by allowing the robot to move the device from the thermocycler to the magnetic bar at the desired times in the process.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for isolating cells, comprising:
providing a plurality of magnetic beads in a first chamber, said magnetic beads capable of binding a cell-specific binding marker so as to attach to a specific cell-type;
providing cells to the first chamber, the cells including cells of the specific cell-type, such that cells of the specific cell-type bind to magnetic beads of the plurality of magnetic beads;
applying a magnetic field to the first chamber to transfer the magnetic beads to a second chamber, the second chamber in fluid communication with the first chamber;
blocking fluid communication between the second chamber and the first chamber;
washing the first chamber;
unblocking fluid communication between the second chamber and the first chamber;
removing the magnetic beads, including the magnetic beads bound to the cells of the specific cell-type, from the second chamber by applying the magnetic field to the second chamber; and
releasing the cells of the specific cell-type from the magnetic beads.

2. The method of claim 1, wherein:
the magnetic field is moveable, optionally wherein the magnetic field is moved in a predetermined direction; and/or
the step of removing the magnetic beads from the second chamber comprises returning the magnetic beads to the first chamber, and further comprises
blocking fluid communication between the second chamber and the first chamber;
washing the second chamber; and
unblocking fluid communication between the second chamber and the first chamber, prior to releasing the cells of the specific cell-type from the magnetic beads.

3. A method for isolating target substrates, comprising:
(a) providing a plurality of magnetic beads to a plurality of respective first chambers, each respective plurality of magnetic beads provided to each first chamber containing only magnetic beads capable of binding to a respective target substrate such that each respective mixing chamber includes magnetic beads capable of binding to only one target substrate type;
(b) providing a sample comprising multiple target substrate types to a plurality of respective first chambers;
(c) applying a magnetic field to transfer the magnetic beads, including any substrates bound thereto, between the first chambers and a second chambers;
(d) blocking fluid communication between the second chambers and the first chambers;
(e) washing select ones of the first chambers and the second chambers to remove non-bound substrates;
(f) unblocking fluid communication between the second chambers and the first chambers;
(g) repeating steps (c)-(f) a predetermined number of times; and
(h) releasing the respective target substrates from the magnetic beads.

4. The method of claim 3, wherein the target substrates comprise peptides, optionally wherein the target substrates are proteins.

5. The method of claim 3, wherein steps (c)-(f) are repeated between one and five times.

6. The method of claim 3, wherein said step of applying a magnetic field comprises bringing a permanent magnet into proximity of the first chambers, optionally wherein the permanent magnet comprises a Rare Earth magnet, optionally a Neodynium magnet.

7. The method of claim 3, wherein said step of applying a magnetic field comprises bringing an electro-magnet into proximity of the first chamber.

8. The method of claim 3, wherein said step of applying a magnetic field comprises activating a stationary magnet, optionally an electromagnet.

9. The method of claim 3, wherein releasing the respective target substrates comprises eluting.

10. The method of claim 3, wherein:
the plurality of first chambers comprises 2 1000 first chambers; and/or each of the first chambers, each of the second chambers or each of the first and second chambers comprises a volume of about 10 nl to about 10 μl.

11. The method of claim 3, wherein the target substrates comprise a molecule, a cell, a DNA, a DNA fragment, a RNA, or an RNA fragment.

12. The method of claim 1, wherein the first chamber and the second chamber are fluid channels of a microfluidic chip.

* * * * *